US007105635B2

(12) United States Patent
Hinman et al.

(10) Patent No.: US 7,105,635 B2
(45) Date of Patent: Sep. 12, 2006

(54) CYCLIC BETA-SHEET PEPTIDES USEFUL AS APOPTOTIC/CYTOTOXIC CANCER AGENTS

(75) Inventors: Channing L. Hinman, Toledo, OH (US); Charles A. Smith, Toledo, OH (US)

(73) Assignee: The University of Toledo, Toledo, OH (US)

( * ) Notice: Subject to any disclaimer, the term of this patent is extended or adjusted under 35 U.S.C. 154(b) by 479 days.

(21) Appl. No.: 10/162,134

(22) Filed: Jun. 4, 2002

(65) Prior Publication Data

US 2003/0224997 A1 Dec. 4, 2003

(51) Int. Cl.
*C07K 5/00* (2006.01)

(52) U.S. Cl. .......................... 530/327; 514/12; 514/14

(58) Field of Classification Search ................ 530/327; 514/14, 12

See application file for complete search history.

(56) References Cited

U.S. PATENT DOCUMENTS

| | | | | |
|---|---|---|---|---|
| 5,164,196 | A | 11/1992 | Plata et al. | |
| 5,232,911 | A * | 8/1993 | Vidal | 514/12 |
| 5,565,431 | A | 10/1996 | Lipps et al. | |
| 6,277,822 | B1 | 8/2001 | Kolbe et al. | |

OTHER PUBLICATIONS

Freshney ,Culture of Animal Cells, A Manual of Basic Technique, Alan R. Liss, Inc., 1983, New York, p. 4.*

Dermer Bio/Technology, 1994, 12:320.*

Gura (Science, 1997, 278:1041-1042.*

Burgess et al, Journal of Cell Biology, vol. 111: Nov. 1990, 2129-2138.*

Lazar et al .,Molecular and Cellular Biology Mar. 1988 vol. 8 No. 3 1247-1252.*

Lin et al .,Biochemistry USA vol. 14:1559-1563 (1975).*

Schwartz et al, Proc Natl Acad Sci USA .vol. 84:6408-6411 (1987).*

Bonny, Christophe; Oberson, Anne; Negri, Stephanie; Sauser, Christelle; Schorderet, Daniel F., *Cell-Permeable Peptide Inhibitors of JNK Novel Blockers of* β-*Cell Death*, (Jan. 2001), Diabetes, vol. 50, pp. 77-82.

Dufton, M.J.; Hider, R.C., *Chapter 7—The Structure and Pharmacology of Elapid Cytotoxins*, (1991), In: Snake Toxins [A.L. Harvey, Ed.] Pergamon Press, Inc., New York, pp. 259-302.

Fernandes, Richard S.; Cotter, Thomas G., (1994), *Apoptosis or Necrosis: Intracellular Levels of Glutathione Influence Mode of Cell Death*, Biochemical Pharamacology, vol. 48, No. 4, pp. 675-681.

Gatineau, E.; Takechi, M.; Bouet, F.; Mansuelle, P.; Rochat, H.; Harvey, A.L.; Montenay-Garestier, Th.; Menez, A., (1990), *Delineation of the Functional Site of a Snake Venom Cardiotoxin: Preparation, Structure, and Function of Monoacetylated Derivatives*, Biochemistry, 29, pp. 6480-6489.

Gatineau E.; Toma, F.; Montenay-Garestier, Th.; Takechi, M.; Fromageot, P.; Menez, A., (1987), *Role of Tyrosine and Tryptophan Residues in the Structure-Activity Relationships of a Cardiotoxin from Naja nigricollis Venom*, Biochemistry, 26, pp. 8046-8055.

Herve, Mireille; Maillere, Bernard; Mourier, Gilles; Texier, Catherine; Leroy, Sandrine; Menez, Andre, (1997), *On the Immunogenic Properties of Retro-Inverso Peptides. Total Retro-Inversion of T-Cell Epitopes Causes a Loss of Binding to MHC II Molecules, Molecular Immunology*, vol. 34, No. 2, pp. 157-163.

Hinman, Channing L.; Jiang, Xiao Ling; Tang, Hai-Ping, (1990), *Selective Cytolysis of a Protein Toxin as a Consequence of Direct Interaction with the Lymphocyte Plasma Membrane*, Toxicology and Applied Pharmacology, 104, pp. 290-300.

Kaneda, Y.; Yamamoto, Y.; Okada, N.; Tsutsuml, Y.; Nakagawa, S.; Kakiuch, M.; Maeda, M.; Kawasaki, K.; Mayumi, T., (1997), *Antimetastatic effect of synthetic Glu-Ile-Leu-Asp-Val peptide derivatives containing D-amino acids*, Anticancer Drugs, Aug; 8(7), pp. 702-707.

Kini, R. Manjunatha; Evans, Herbert J., (1989), *Role of Cationic Residues in Cytolytic Activity: Modification of Lysine Residues in the Cardiotoxin from Naja nigricollis Venom and Correlation between Cytolytic and Antiplatelet Activity*, Biochemistry, 28, pp. 9209-9215.

Lin, Shinne-Ren; Chang, Kee-Lung; Chang, Chun-Chang, (Sep. 1993), *Chemical Modification of Amino Groups in Cardiotoxin III from Taiwan Cobra* (*Naja Naja Atra*) *Venom*, Biochemistry and Molecular Biology International, vol. 31, No. 1, pp. 175-184.

Martin, Seamus J.; Reutelingsperger, Chris P.M.; McGahon, Anne J.; Rader, James A.; van Schie, Rob C.A.A.; LaFace, Drake M., (Nov. 1995), *Early Redistribution of Plasma Membrane Phosphatidylserine is a General Feature of Apoptosis Regardless of the Initiating Stimulus: Inhibition by Overexpression of Bel-2 and Abl*, J. Exp. Med., vol. 182, pp. 1545-1556.

Stevens-Truss, R.; Messer, Jr., W.S.; Hinman, C.L., (1996), *Heart and T-Lymphoctye Cell Surfaces Both Exhibit Positive Cooperativity in Binding a Membrane-Lytic Toxin*, J. Membrane Biol., 150, pp. 113-122.

Stevens-Truss, Regina; Hinman, Channing L., (1996), *Chemical Modification of Methionines in a Cobra Venom Cytotoxin Differentiates between Lytic and Binding Domains*, Toxicology and Applied Pharmacology, 139, pp. 234-242.

Stevens-Truss, Regina; Hinman, Channing L., (1997), *Activities of Cobra Venom Cytotoxins Toward Heart and Leukemic T-Cells Depend on Localized Amino Acid Differences*, Toxicon, vol. 35, No. 5, pp. 659-669.

Van Regenmortel, Marc HV; Muller, Sylviane, (1998), *D-peptides as immunogens and diagnostic reagents*, Protein Engineering, 9, pp. 377-382.

Zhang, Guohong; Gurtu, Vanessa; Kain, Steven R.; Yan, Guochen, (Sep. 1997), *Early Detection of Apoptosis Using a Fluorescent Conjugate of Annexin V*, BioTechniques, 23, pp. 525-531.

Smith, C.A., *Thesis: The Importance of Cardiotoxin Atra III Synthetic Peptide Loop 1 Amino Acid Residues Asparagine 4 and Tyrosine 11 in Relation to Anti-Cancer Activity and Binding to Leukemic T-cell Membrane Surface Receptor*, submitted Dec. 2000, not published until Jun. 7, 2001.

* cited by examiner

*Primary Examiner*—Sheela J. Huff

(74) *Attorney, Agent, or Firm*—MacMillan, Sobanski & Todd, LLC

(57) ABSTRACT

Peptides and pharmaceutical compositions of matter useful as cytotoxic compositions particularly for, but not limited to, treatment of cancers, that includes a synthetic peptide whose amino acid sequence is different from an initial loop of cobra cardiotoxin.

11 Claims, 11 Drawing Sheets

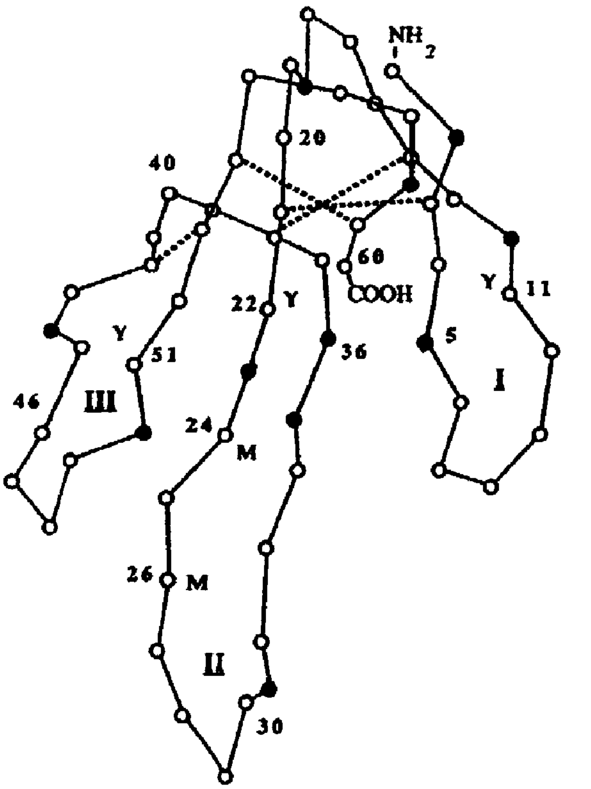
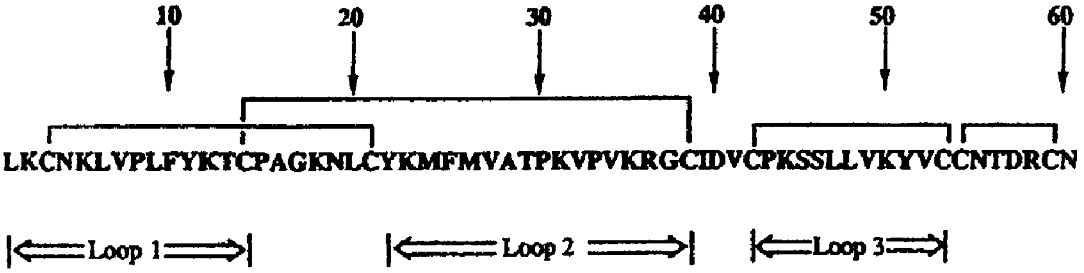
Figure 1

Figure 4
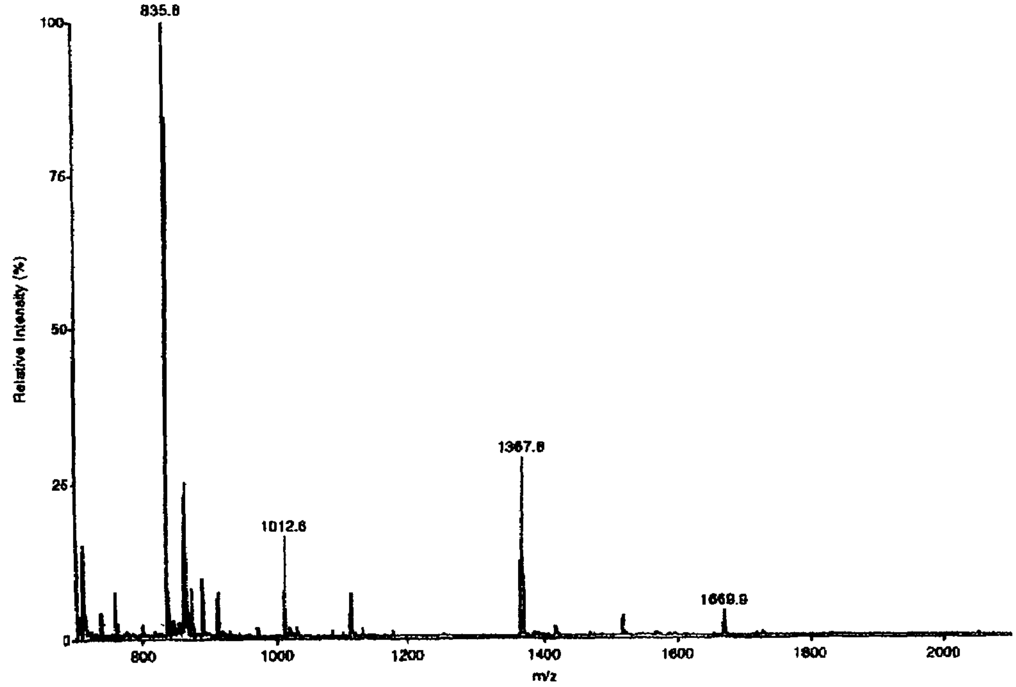
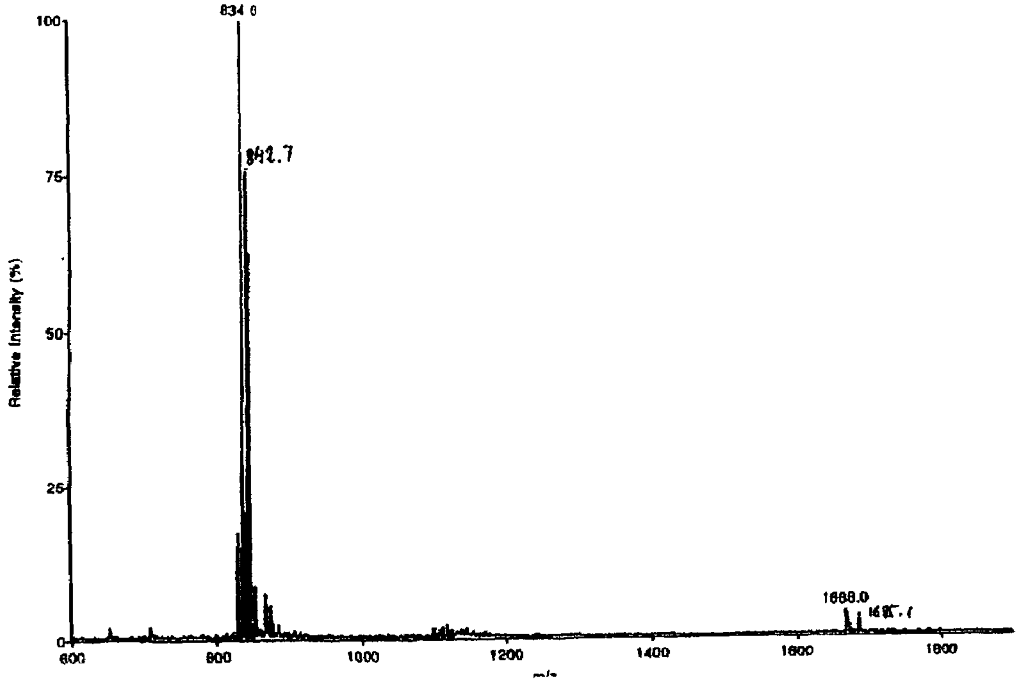
Figure 5

Figure 6. L1AD3 Computational Molecular Model Image.

Figure 7. Superimposition of LIN-KA D3 with LIA D3.

Figure 10a
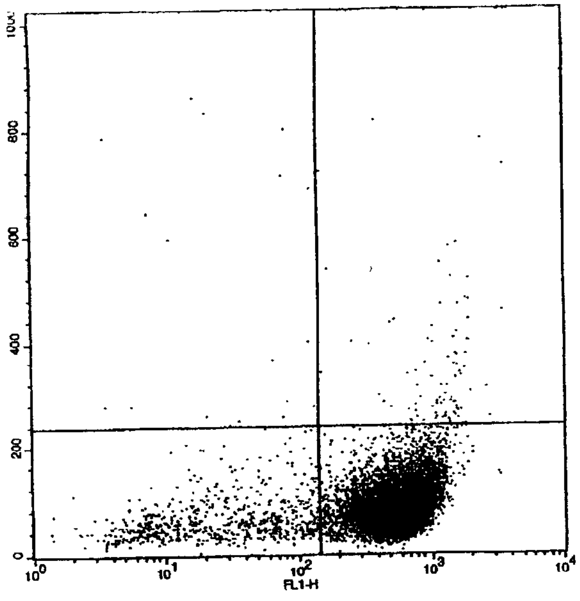
Figure 10b
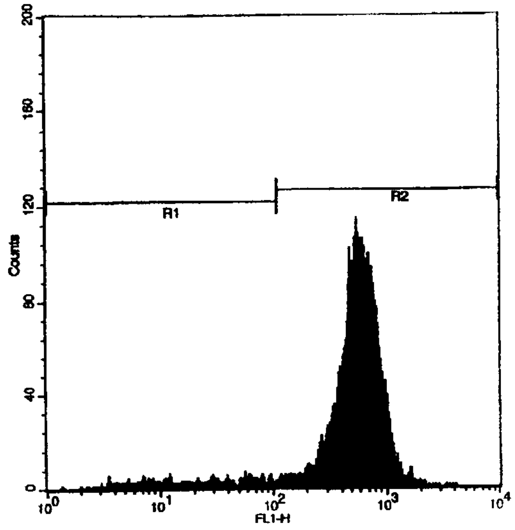
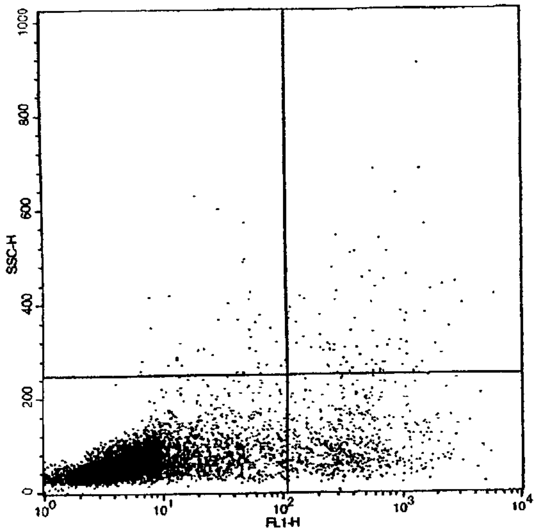
Figure 10c
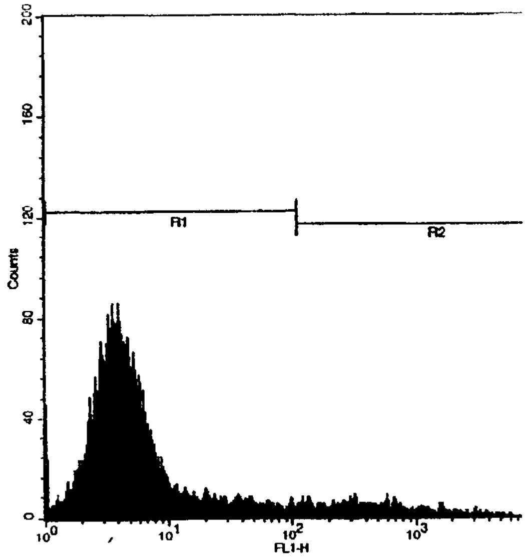
Figure 10d

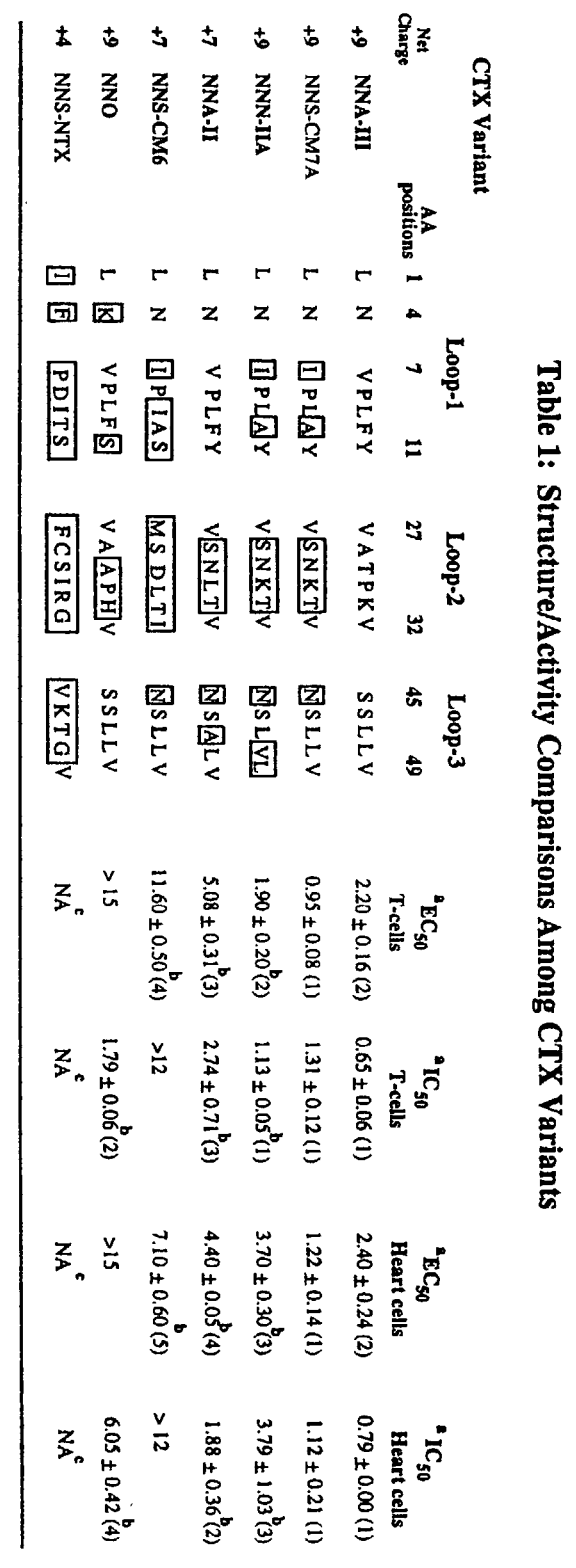

Table 1: Structure/Activity Comparisons Among CTX Variants

| Net Charge | CTX Variant | AA positions 1 | 4 | Loop-1 7 11 | Loop-2 27 32 | Loop-3 45 49 | [a]$EC_{50}$ T-cells | [a]$IC_{50}$ T-cells | [a]$EC_{50}$ Heart cells | [a]$IC_{50}$ Heart cells |
|---|---|---|---|---|---|---|---|---|---|---|
| +9 | NNA-III | L | N | V P L F Y | V A T P K V | S S L L V | 2.20 ± 0.16 (2) | 0.65 ± 0.06 (1) | 2.40 ± 0.24 (2) | 0.79 ± 0.00 (1) |
| +9 | NNS-CM7A | L | N | I P L A Y | V S N K T V | N S L L V | 0.95 ± 0.08 (1) | 1.31 ± 0.12 (1) | 1.22 ± 0.14 (1) | 1.12 ± 0.21 (1) |
| +9 | NNN-IIA | L | N | I P L A Y | V S N K T V | N S L V L | 1.90 ± 0.20[b] (2) | 1.13 ± 0.05[b] (1) | 3.70 ± 0.30[b] (3) | 3.79 ± 1.03[b] (3) |
| +7 | NNA-II | L | N | V P L F Y | V S N L T V | N S A L V | 5.08 ± 0.31[b] (3) | 2.74 ± 0.71[b] (3) | 4.40 ± 0.05[b] (4) | 1.88 ± 0.36[b] (2) |
| +7 | NNS-CM6 | L | N | I P I A S | M S D L T I | N S L L V | 11.60 ± 0.50[b] (4) | >12 | 7.10 ± 0.60[b] (5) | > 12 |
| +9 | NNO | L | K | V P L F S | V A A P H V | S S L L V | > 15 | 1.79 ± 0.06[b] (2) | >15 | 6.05 ± 0.42[b] (4) |
| +4 | NNS-NTX | I | F | P D I T S | F C S I R G | V K T G V | NA[c] | NA[c] | NA[c] | NA[c] |

Figure 14

SEQUENCE LISTING

```
<160> NUMBER OF SEQ ID NOS: 19

<210> SEQ ID NO 1
<211> LENGTH: 14
<212> TYPE: PRT
<213> ORGANISM: Artificial Sequence
<220> FEATURE:
<223> OTHER INFORMATION: THIS PEPTIDE, NAMED L1AD3, HAS A DISULFIDE BOND
      BETWEEN ITS ONLY Cys RESIDUES, FOR WHICH OCCUR AT POSITION NOS.
      3 AND 14, RESPECTIVELY.
<220> FEATURE:
<221> NAME/KEY: DISULFID
<222> LOCATION: (3)..(14)
```

-continued

```
<223> OTHER INFORMATION:
<300> PUBLICATION INFORMATION:
<301> AUTHORS: Smith, Charles A.
<302> TITLE: The Importance of Cardiotoxin Atra III Synthetic Peptide
      Loop/Amino Acid Residues Asparagine 4 and Tyrosine 11 in Relation
      to Anticancer Activity and Binding to Leukemic T-Cell Membrane
      Surface Receptor
<306> PAGES: 1-247
<307> DATE: 2001-06-07
<308> DATABASE ACCESSION NUMBER: Dissertation Abstracts International,
      Publication No. 9990665
<309> DATABASE ENTRY DATE: 2001-03-01

<400> SEQUENCE: 1

Leu Lys Cys Asn Lys Leu Val Pro Leu Phe Tyr Lys Thr Cys
1               5                   10


<210> SEQ ID NO 2
<211> LENGTH: 14
<212> TYPE: PRT
<213> ORGANISM: Artificial Sequence
<220> FEATURE:
<223> OTHER INFORMATION: At position 7 of L1AD3, Val replaced by Ile
<220> FEATURE:
<221> NAME/KEY: DISULFID
<222> LOCATION: (3)..(14)
<223> OTHER INFORMATION:

<400> SEQUENCE: 2

Leu Lys Cys Asn Lys Leu Ile Pro Leu Phe Tyr Lys Thr Cys
1               5                   10


<210> SEQ ID NO 3
<211> LENGTH: 14
<212> TYPE: PRT
<213> ORGANISM: Artificial Sequence
<220> FEATURE:
<223> OTHER INFORMATION: At positions 7 and 10 in L1AD3, Val is
      replaced by Ile, and Phe is replaced by Ala, respectively
<220> FEATURE:
<221> NAME/KEY: DISULFID
<222> LOCATION: (3)..(14)
<223> OTHER INFORMATION:

<400> SEQUENCE: 3

Leu Lys Cys Asn Lys Leu Ile Pro Leu Ala Tyr Lys Thr Cys
1               5                   10


<210> SEQ ID NO 4
<211> LENGTH: 14
<212> TYPE: PRT
<213> ORGANISM: Artificial Sequence
<220> FEATURE:
<223> OTHER INFORMATION: At position 10 in L1AD3, F is changed to A
<220> FEATURE:
<221> NAME/KEY: DISULFID
<222> LOCATION: (3)..(14)
<223> OTHER INFORMATION:

<400> SEQUENCE: 4

Leu Lys Cys Asn Lys Leu Val Pro Leu Ala Tyr Lys Thr Cys
1               5                   10


<210> SEQ ID NO 5
<211> LENGTH: 14
<212> TYPE: PRT
<213> ORGANISM: Artificial Sequence
<220> FEATURE:
<223> OTHER INFORMATION: At position 4 in L1AD3, N is changed to Q
<220> FEATURE:
<221> NAME/KEY: DISULFID
```

-continued

<222> LOCATION: (3)..(14)
<223> OTHER INFORMATION:
<300> PUBLICATION INFORMATION:
<301> AUTHORS: Smith, Charles A.
<302> TITLE: The Importance of Cardiotoxin Atra III Synthetic Peptide Loop/Amino Acid Residues Asparagine 4 and Tyrosine 11 in Relation to Anticancer Activity and Binding to Leukemic T-Cell Membrane Surface Receptor
<306> PAGES: 1-247
<307> DATE: 2001-06-07
<308> DATABASE ACCESSION NUMBER: Dissertation Abstracts International, Publication No. 9990665
<309> DATABASE ENTRY DATE: 2001-03-01

<400> SEQUENCE: 5

Leu Lys Cys Gln Lys Leu Val Pro Leu Phe Tyr Lys Thr Cys
1 5 10

<210> SEQ ID NO 6
<211> LENGTH: 14
<212> TYPE: PRT
<213> ORGANISM: Artificial Sequence
<220> FEATURE:
<223> OTHER INFORMATION: D-amino acid versions of L1AD3 VARIANTS
<220> FEATURE:
<221> NAME/KEY: DISULFID
<222> LOCATION: (1)..(12)
<223> OTHER INFORMATION:

<400> SEQUENCE: 6

Cys Thr Lys Tyr Phe Leu Pro Val Leu Lys Asn Cys Lys Leu
1 5 10

<210> SEQ ID NO 7
<211> LENGTH: 14
<212> TYPE: PRT
<213> ORGANISM: Artificial Sequence
<220> FEATURE:
<223> OTHER INFORMATION: At the L-position 7, V is changed to I in the D-form of L1AD3
<220> FEATURE:
<221> NAME/KEY: DISULFID
<222> LOCATION: (1)..(12)
<223> OTHER INFORMATION:

<400> SEQUENCE: 7

Cys Thr Lys Tyr Phe Leu Pro Ile Leu Lys Asn Cys Lys Leu
1 5 10

<210> SEQ ID NO 8
<211> LENGTH: 14
<212> TYPE: PRT
<213> ORGANISM: Artificial Sequence
<220> FEATURE:
<223> OTHER INFORMATION: At the L-position 7, V is changed to I, and at L-10, F is changed to A in the D-form of L1AD3
<220> FEATURE:
<221> NAME/KEY: DISULFID
<222> LOCATION: (1)..(12)
<223> OTHER INFORMATION:

<400> SEQUENCE: 8

Cys Thr Lys Tyr Ala Leu Pro Ile Leu Lys Asn Cys Lys Leu
1 5 10

<210> SEQ ID NO 9
<211> LENGTH: 14
<212> TYPE: PRT
<213> ORGANISM: Artificial Sequence
<220> FEATURE:
<223> OTHER INFORMATION: At L-position 10, F is changed to A in the -continued D-form of L1AD3
<220> FEATURE:
<221> NAME/KEY: DISULFID
<222> LOCATION: (1)..(12)
<223> OTHER INFORMATION:

<400> SEQUENCE: 9

Cys Thr Lys Tyr Ala Leu Pro Val Leu Lys Asn Cys Lys Leu
1 5 10

<210> SEQ ID NO 10
<211> LENGTH: 14
<212> TYPE: PRT
<213> ORGANISM: Artificial Sequence
<220> FEATURE:
<223> OTHER INFORMATION: At L-position 4, N is changed to Q in the D-form of L1AD3
<220> FEATURE:
<221> NAME/KEY: DISULFID
<222> LOCATION: (1)..(12)
<223> OTHER INFORMATION:

<400> SEQUENCE: 10

Cys Thr Lys Tyr Phe Leu Pro Val Leu Lys Gln Cys Lys Leu
1 5 10

<210> SEQ ID NO 11
<211> LENGTH: 60
<212> TYPE: PRT
<213> ORGANISM: Naja naja atra

<400> SEQUENCE: 11

Leu Lys Cys Asn Lys Leu Val Pro Leu Phe Tyr Lys Thr Cys Pro Ala
1 5 10 15

Gly Lys Asn Leu Cys Tyr Lys Met Phe Met Val Ala Thr Pro Lys Val
20 25 30

Pro Val Lys Arg Gly Cys Ile Asp Val Cys Pro Lys Ser Ser Leu Leu
35 40 45

Val Lys Tyr Val Cys Cys Asn Thr Asp Arg Cys Asn
50 55 60

<210> SEQ ID NO 12
<211> LENGTH: 14
<212> TYPE: PRT
<213> ORGANISM: Artificial Sequence
<220> FEATURE:
<223> OTHER INFORMATION: The N-terminal Leu is biotinylated during synthesis in L1AD3
<220> FEATURE:
<221> NAME/KEY: MISC
<222> LOCATION: (1)..(14)
<223> OTHER INFORMATION:
<300> PUBLICATION INFORMATION:
<301> AUTHORS: Smith, Charles A.
<302> TITLE: The Importance of Cardiotoxin Atra III Synthetic Peptide Loop/Amino Acid Residues Asparagine 4 and Tyrosine 11 in Relation to Anticancer Activity and Binding to Leukemic T-Cell Membrane Surface Receptor
<306> PAGES: 1-247
<307> DATE: 2001-06-07
<308> DATABASE ACCESSION NUMBER: Dissertation Abstracts International, Publication No. 9990665
<309> DATABASE ENTRY DATE: 2001-03-01

<400> SEQUENCE: 12

Leu Lys Cys Asn Lys Leu Val Pro Leu Phe Tyr Lys Thr Cys
1 5 10

-continued

```
<210> SEQ ID NO 13
<211> LENGTH: 14
<212> TYPE: PRT
<213> ORGANISM: Artificial Sequence
<220> FEATURE:
<223> OTHER INFORMATION: At position 11, Y is changed to S in L1AD3
<220> FEATURE:
<221> NAME/KEY: DISULFID
<222> LOCATION: (3)..(14)
<223> OTHER INFORMATION:
<300> PUBLICATION INFORMATION:
<301> AUTHORS: Smith, Charles A.
<302> TITLE: The Importance of Cardiotoxin Atra III Synthetic Peptide
      Loop/Amino Acid Residues Asparagine 4 and Tyrosine 11 in Relation
      to Anticancer Activity and Binding to Leukemic T-Cell Membrane
      Surface Receptor
<306> PAGES: 1-247
<307> DATE: 2001-06-07
<308> DATABASE ACCESSION NUMBER: Dissertation Abstracts International,
      Publication No. 9990665
<309> DATABASE ENTRY DATE: 2001-03-01

<400> SEQUENCE: 13

Leu Lys Cys Asn Lys Leu Val Pro Leu Phe Ser Lys Thr Cys
1               5                   10


<210> SEQ ID NO 14
<211> LENGTH: 14
<212> TYPE: PRT
<213> ORGANISM: Artificial Sequence
<220> FEATURE:
<223> OTHER INFORMATION: At position 11, Y is changed to F in L1AD3
<220> FEATURE:
<221> NAME/KEY: DISULFID
<222> LOCATION: (3)..(14)
<223> OTHER INFORMATION:
<300> PUBLICATION INFORMATION:
<301> AUTHORS: Smith, Charles A.
<302> TITLE: The Importance of Cardiotoxin Atra III Synthetic Peptide
      Loop/Amino Acid Residues Asparagine 4 and Tyrosine 11 in Relation
      to Anticancer Activity and Binding to Leukemic T-Cell Membrane
      Surface Receptor
<306> PAGES: 1-247
<307> DATE: 2001-06-07
<308> DATABASE ACCESSION NUMBER: Dissertation Abstracts International,
      Publication No. 9990665
<309> DATABASE ENTRY DATE: 2001-03-01

<400> SEQUENCE: 14

Leu Lys Cys Asn Lys Leu Val Pro Leu Phe Phe Lys Thr Cys
1               5                   10


<210> SEQ ID NO 15
<211> LENGTH: 14
<212> TYPE: PRT
<213> ORGANISM: Artificial Sequence
<220> FEATURE:
<223> OTHER INFORMATION: At position 11, Y is changed to W in L1AD3
<220> FEATURE:
<221> NAME/KEY: DISULFID
<222> LOCATION: (3)..(14)
<223> OTHER INFORMATION:
<300> PUBLICATION INFORMATION:
<301> AUTHORS: Smith, Charles A.
<302> TITLE: The Importance of Cardiotoxin Atra III Synthetic Peptide
      Loop/Amino Acid Residues Asparagine 4 and Tyrosine 11 in Relation
      to Anticancer Activity and Binding to Leukemic T-Cell Membrane
      Surface Receptor
<306> PAGES: 1-247
<307> DATE: 2001-06-07
<308> DATABASE ACCESSION NUMBER: Dissertation Abstracts International,
      Publication No.  9990665
<309> DATABASE ENTRY DATE: 2001-03-01

<400> SEQUENCE: 15
```

-continued

Leu Lys Cys Asn Lys Leu Val Pro Leu Phe Trp Lys Thr Cys
1 5 10

<210> SEQ ID NO 16
<211> LENGTH: 14
<212> TYPE: PRT
<213> ORGANISM: Artificial Sequence
<220> FEATURE:
<223> OTHER INFORMATION: At position 4, N is changed to K in L1AD3
<220> FEATURE:
<221> NAME/KEY: DISULFID
<222> LOCATION: (3)..(14)
<223> OTHER INFORMATION:
<300> PUBLICATION INFORMATION:
<301> AUTHORS: Smith, Charles A.
<302> TITLE: The Importance of Cardiotoxin Atra III Synthetic Peptide Loop/Amino Acid Residues Asparagine 4 and Tyrosine 11 in Relation to Anti-Cancer Activity and Binding to Leukemic T-Cell Membrane Surface Receptor
<306> PAGES: 1-247
<307> DATE: 2001-06-07
<308> DATABASE ACCESSION NUMBER: Dissertation Abstracts International, Publication No. 9990665
<309> DATABASE ENTRY DATE: 2001-03-01

<400> SEQUENCE: 16

Leu Lys Cys Lys Lys Leu Val Pro Leu Phe Tyr Lys Thr Cys
1 5 10

<210> SEQ ID NO 17
<211> LENGTH: 14
<212> TYPE: PRT
<213> ORGANISM: Artificial Sequence
<220> FEATURE:
<223> OTHER INFORMATION: At position 4, N is changed to H in L1AD3
<220> FEATURE:
<221> NAME/KEY: DISULFID
<222> LOCATION: (3)..(14)
<223> OTHER INFORMATION:
<300> PUBLICATION INFORMATION:
<301> AUTHORS: Smith, Charles A.
<302> TITLE: The Importance of Cardiotoxin Atra III Synthetic Peptide Loop/Amino Acid Residues Asparagine 4 and Tyrosine 11 in Relatio to Anticancer Activity and Binding to Leukemic T-Cell Membrane Surface Receptor
<306> PAGES: 1-247
<307> DATE: 2001-06-07
<308> DATABASE ACCESSION NUMBER: Dissertation Abstracts International, Publication No. 9990665
<309> DATABASE ENTRY DATE: 2001-03-01

<400> SEQUENCE: 17

Leu Lys Cys His Lys Leu Val Pro Leu Phe Tyr Lys Thr Cys
1 5 10

<210> SEQ ID NO 18
<211> LENGTH: 14
<212> TYPE: PRT
<213> ORGANISM: Artificial Sequence
<220> FEATURE:
<223> OTHER INFORMATION: At position 4, N is changed to K, and at position 11, Y is changed to S in L1AD3
<220> FEATURE:
<221> NAME/KEY: DISULFID
<222> LOCATION: (3)..(14)
<223> OTHER INFORMATION:
<300> PUBLICATION INFORMATION:
<301> AUTHORS: Smith, Charles A.
<302> TITLE: The Importance of Cardiotoxin Atra III Synthetic Peptide Loop/Amino Acid Residues Asparagine 4 and Tyrosine 11 in Relatio to Anticancer Activity and Binding to Leukemic T-Cell Membrane Surface Receptor
<306> PAGES: 1-247

-continued

```
<307> DATE: 2001-06-07
<308> DATABASE ACCESSION NUMBER: Dissertation Abstracts International,
      Publication No. 9990665
<309> DATABASE ENTRY DATE: 2001-03-01

<400> SEQUENCE: 18

Leu Lys Cys Lys Lys Leu Val Pro Leu Phe Ser Lys Thr Cys
1               5                   10


<210> SEQ ID NO 19
<211> LENGTH: 15
<212> TYPE: PRT
<213> ORGANISM: Naja naja kaouthia

<400> SEQUENCE: 19

Met Glu Cys Tyr Arg Met Ser Asn Ile Val Thr Cys Gln Pro Trp
1               5                   10                  15
```

CYCLIC BETA-SHEET PEPTIDES USEFUL AS APOPTOTIC/CYTOTOXIC CANCER AGENTS

TECHNICAL FIELD OF THE INVENTION

The present invention relates to cyclic anti-parallel beta-sheet peptide compositions that cause apoptosis in cancer cells. The peptide compositions are useful to selectively kill cells such as T-lymphocytes in disease states such as cancer, HIV-1 infection, or autoimmunity.

The peptide compositions comprise at least one synthetic analog of the first loop of cobra venom cytotoxins/cardiotoxins. The peptide compositions contain hydrophobic amino acids, including tyrosine, as well as positively charged amino acids. The small peptide compositions have a molecular mass less than 2000 Daltons and are cyclized by the formation of a single disulfide bond. Their structure has no alpha helical components, but contains two apposed beta strands connected by a short string of amino acids.

The peptide composition is not toxic toward normal human white blood cells; in contrast to the three-loop naturally occurring toxin, the peptide composition of the present invention does not depolarize heart muscle. The peptide composition binds a protein receptor on the surface of leukemic T-lymphocytes, which receptor is especially useful as a target for other chemotherapeutic agents that can be coupled to this peptide or derivatives thereof.

BACKGROUND OF THE INVENTION

Several distinct cytotoxins can be isolated from any given cobra venom sample, and more than 50 variants have been sequenced (Dufton and Hider, 1991). These cobra cytotoxins are polybasic, yet hydrophobic proteins, typically consisting of 60 amino acids, with a molecular weight of 6000–7000 Daltons. Crystallographic and nuclear magnetic resonance (NMR) analysis indicates that these proteins contain no alpha helical structure, but rather consist of three loops of anti-parallel beta strands emanating from a core that is constrained by four disulfide bonds, as shown in FIG. 1. Structural features thought to be responsible for their activity involve rather flat beta sheet regions of hydrophobic residues flanked by cationic amino acids (Kini & Evans, 1989). These toxins induce rapid depolarization of skeletal and cardiac muscle. Some of the toxins are selectively cytotoxic for a variety of human cancer cell lines. Previous comparisons of native toxins indicated that *Naja naja atra* III cytotoxin (hereinafter abbreviated as CTX) was highly toxic toward human leukemic T-lymphocytes, whereas the toxin from *Naja naja oxiana* displayed almost no toxicity, even though the two proteins differed at only 4 of their 60 residues. Moreover, two of these differences occurred in the first loop (Stevens-Truss & Hinman, 1997).

Chemical modifications of individual amino acids have contributed toward an elucidation of structural features that may underlie cytotoxicity. After separation of toxins modified by acetylation of individual lysine residues, Lin, Chang & Chang (1993) and Gatineau et al. (1990) reported that the most critical lysine was at position 12 in the first loop of cytotoxin. Earlier, Gatineau et al. (1987) using nitration of tyrosine, indicated that the tyrosine at position 11 in Loop 1 was the most important of the three tyrosines in the molecule. From other studies, it has been suggested that cardiotoxicity, as opposed strictly to cytotoxicity, depends upon amino acid residues in loops 2 and 3.

Previous work by the inventors herein involving synthetic analogs of each of the three loops of cytotoxin III from *Naja naja atra* has shown than a Loop 2 construct, in which the Cys at position 21 forms an unusual disulfide bond with the Cys at position 38 (FIG. 1), had no activity against either heart cells or against human tumor T-lymphocytes (the CEM line). By contrast, the Loop 1 analog, in which the Cys at position 3 is constrained to form a disulfide bond with the Cys at position 14 (FIG. 1), was highly active in its ability to inhibit thymidine incorporation in CEM tumor cells.

Two prior patents have been found that involve components of cobra venom. The first, Vidal, U.S. Pat. No. 5,232,911 issued in 1993, utilized a whole cardiotoxin reported to have been purified from *N. n. atra,* but whose indicated sequence has an extra alanine within the first 15 residues and which more closely resembles toxins from *Naja haje* or from *Naja nivea* (Dufton and Hider, 1991). This 61-amino acid protein was for use in cancer chemotherapy strictly as an enhancer of the phospholipase activity of a heterodimer isolated from another snake, *Crotalus durissus terrificus.* The only application of the *N. n. atra* peptide was when it would be administered in combination with the much larger heterodimer. The Lipps et al. U.S. Pat. No. 5,565,431 issued in 1996, involved a toxin isolated from the Thailand cobra, *Naja naja* Kaouthia, which the inventors termed "Kaotree." Having a reported molecular weight based on gel electrophoresis of approximately 6000 Daltons, the sequence of its first 15 amino acids [using single-letter abbreviations: MECYRMSNIVTCQPW] Seq. ID No. 19, is very much different from the sequence of any of the cardiotoxins from *N. n. siamensis* (Kaouthia) [or for any of the 50+ cardiotoxins reported by Dufton and Hider (1991)].

OBJECTS OF THE INVENTION

It is an object of this invention to provide a cytotoxic agent that prevents the proliferation of cancer cells, and in particular, leukemic T-cells.

It is another object of this invention to provide a cytotoxic agent that exhibits minimal toxic effects against normal human cells.

It is a further object of this invention to provide a cytotoxic agent that induces apoptosis as a mechanism of causing cell death.

It is yet another object of this invention to provide an agent that binds a protein receptor, which receptor itself is useful as a target for the delivery of other chemotherapeutic agents.

It is an object of this invention to provide an agent that serves as a lead compound for development of selective cytotoxic agents, based upon its unique structural features.

DESCRIPTION OF THE DRAWINGS

FIG. 1 is a schematic representation of cobra cytotoxin. The three primary loops are indicated by underlined Roman numerals. Four disulfide bonds are represented by dashed lines joining circles. Individual amino acids are shown as circles. Positively charged side chains of lysine and arginine are shown as filled circles. Below is the amino acid sequence of CTX, Seq. ID No. 11, indicating the loop organization and the residues that form disulfide bonds (from Dufton and Hider, 1991).

FIGS. 4 and 5 are electrospray mass spectrographic analyses of the linear (FIG. 4) and cyclized (FIG. 5) L1AD3 peptide. The $M^{+1}$ ion peak for linear L1AD3 is at 1669.9 and its $M^{+2}$ ion peak is at 835.6. These are the peaks for the 1,668 Dalton mass of the linear peptide. The $M^{+1}$ ion peak for cyclized L1AD3 is at 1668.0 and its $M^{+2}$ ion peak is at 834.6. These are the peaks for the 1,666 Dalton mass of the cyclized peptide and reflect the loss of two protons incurred during disulfide bond formation between cysteine side chains.

FIGS. 10*a–d* are graphs showing comparisons of phosphatidyl serine exposure on the outer surface of CEM cells following a 2.5-hour incubation with or without 40 μM cyclized L1AD3. After incubation, cells were washed twice with cold PBS prior to adding FITC-conjugated Annexin-V. Flow cytometry using a B-D FACSCalibur was performed, and 10,000 cells were analyzed using the B-D CellQuest program. Individual cells are represented in the dot plots on the left (FIGS. 10*a* and 10*c*), and histograms of the same data are on the right (FIGS. 10*b* and *d*). Whereas untreated tumor cells show less than 6% spontaneous apoptosis (FIG. 10*c,* lower left quadrant), 93% of cells treated with L1AD3 undergo apoptosis after 2.5 hours (FIG. 10*d,* lower right quadrant).

FIG. 14 is a table showing the structure and activity comparisons among CTX variants. a: μM+S.E. Numbers in parentheses give the $EC_{50}$ or $IC_{50}$ rank order (1=most potent or strongest affinity) of CTX variants for both cell types with the same numbers indicating no significant difference (P>0.05, determined by Tukey analysis). $EC_{50}$ values were determined from three experiments performed in duplicate; $IC_{50}$ values were determined from two experiments performed in triplicate. b: Values are significantly different, when comparing one cell type to the other (P<0.05, determined by ANOVA for simple effects. c: NA=not attained. Single letter abbreviations are used for individual amino acids. Boxed residues indicate the amino acids which differ from those of *Naja naja atra* cytotoxin-III (CTX), whose sequence is: LKCNKLVPLFYKTCPAGKNLCYKMFMVATPKVPVKRGCIDVCPKSSLL VKYVCCNTDRCN, Seq. ID No. 11.

DESCRIPTION OF THE PREFERRED EMBODIMENT

Figure 2:
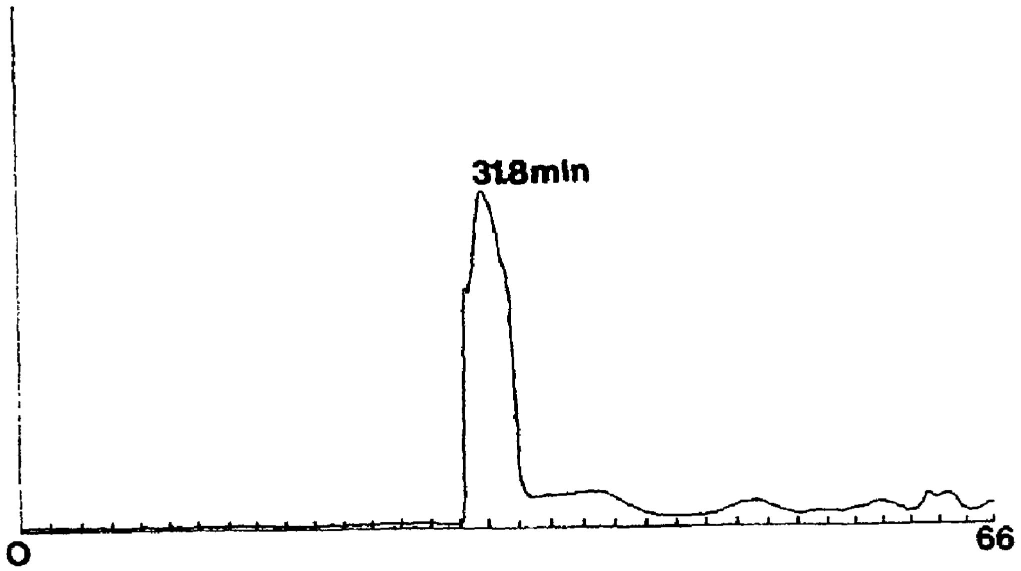
FIG. 2 is an HPLC chromatogram of the linear L1AD3 peptide. The x-axis indicates elution time in minutes, and the y-axis represents absorbance at 280 nm. The retention time of the peptide is printed above the major peak. Elution was accomplished using a 30% to 100% linear gradient over 60 minutes consisting of 3:1 acetonitrile/2-propanol with 0.1% TFA versus 0.1% TFA in water.

The present invention relates to a synthetic peptide whose amino acid sequence is different from loop 1 of a cobra cardiotoxin in which a disulfide bond occurs between two Cys residues and to a pharmaceutical composition of matter containing such peptide, which composition is useful as a cytotoxic agent.

In a particular aspect, the present invention relates to the peptides as shown in Seq. ID Nos. 1, 2, 3, 4, 5, 6, 7, 8, 9, 10, and 12.

The present invention also relates to a method for treatment of cancer, including for example T-Cell or B-Cell leukemia, T-cell based autoimmune diseases, or for destruction of HIV-1-infected T-lymphocytes comprising administering an efficacious dose of at least one therapeutic agent which comprises the peptide or an analog or a derivative of the peptide of the present invention.

In one aspect the present invention relates to a pharmaceutical composition of matter useful as a cytotoxic agent comprising a peptide whose amino acid sequence comprises one of the following sequences: Leu-Lys-Cys-4-Lys-Leu-7-Pro-Leu-10-Tyr-Lys-Thr-Cys, where 4 is Asn or Gln; 7 is Val or Ile; 10 is Phe or Ala. The composition has a disulfide bond between the $Cys^3$ and $Cys^{14}$ residues.

In another aspect, the present invention relates to a cytotoxic composition that induces apoptosis comprising at least one of the peptides of the present invention.

In still another aspect, the present invention relates to a method of making the peptides of Seq. ID Nos. 6, 7, 8, 9, and 10 in which the D-amino acid peptide is synthesized sequentially in an opposite direction from that of the L-amino acid peptide, wherein the opposite direction is from amino terminus to carboxyl terminus.

The peptides of the present invention (the L1AD3) (and its other variations mentioned here) do not occur naturally. These peptides and their variations are synthetic constructs and differ from the original natural compound in that: (i) they are smaller, and (ii) the location and the orientation of the single disulfide bond are different from either of the two disulfide bonds within loop 1 of cobra cardiotoxin, in which the same $^3$Cys and $^{14}$Cys residues participate. More specifically, although the amino acid sequence that comprises this synthetic peptide is derived from a larger cardiotoxin molecule, the two cysteines in the synthetic compound are oxidized to form a loop with a unique $^3$Cys-s-s-$^{14}$Cys disulfide bond. Therefore, the synthetic peptides, as well as the other variations mentioned herein, are non-natural and distinct from any region of the naturally occurring cardiotoxin.

The synthetic peptide compositions of the present invention are active by themselves, without the remaining 46 amino acids of a whole cobra cardiotoxin. The cyclic structure involves a disulfide bond between residues 3 and 14, rather than between residues 3 and 21, as found in the native toxins.

In one aspect, the present invention relates to peptide compositions, including in particular, the peptide called L1AD3, which are novel compounds useful as cancer chemotherapeutic agents and/or as lead compounds for the development of other therapeutic agents. The L1AD3 has the sequence: Leu-Lys-Cys-Asn-Lys-Leu-Val-Pro-Leu-Phe-Tyr-Lys-Thr-Cys [single letter code LKCNKLVPLFYKTC], Seq. ID No. 1. This peptide has a disulfide bond between the Cys residues, which occur at positions 3 and 4.

In another aspect of the present invention, the present invention relates to additional variations of the above peptides with replacements of at least single amino acid residues. The peptides are believed to have essentially the same activity as the L1AD3 peptide. These peptide variations include, but are not limited to:

Leu-Lys-Cys-Asn-Lys-Leu-Ile-Pro-Leu-Phe-Tyr-Lys-Thr-Cys [single letter code: LKCNKLIPLFYKTC] Seq. ID No. 2, where, at position 7, Val is replaced by Ile in Seq. ID No. 1.

Leu-Lys-Cys-Asn-Lys-Leu-Ile-Pro-Leu-Ala-Tyr-Lys-Thr-Cys [single letter code: LKCNKLIPLAYKTC] Seq. ID No. 3, where, at position 7, Val is replaced by Ile and at position 10, Phe is replaced by Ala in Seq. ID no. 1.

Leu-Lys-Cys-Asn-Lys-Leu-Val-Pro-Leu-Ala-Tyr-Lys-Thr-Cys [single letter code: LKCNKLVPLAYKTC] Seq. ID No. 4, where, at position 10, Phe is replaced by Ala in Seq. ID No. 1.

Leu-Lys-Cys-Gln-Lys-Leu-Val-Pro-Leu-Phe-Tyr-Lys-Thr-Cys [single letter code: LKCQKLVPLFYKTC] Seq. ID No. 5 where, at position 4, Asn is replaced by Gln in Seq. ID no. 1.

In still another aspect, the present invention relates to other constructs of these peptides, which have the same amino acid composition and sequence as those discussed above, with the exception that these peptides are synthesized with and composed of D-amino acids instead of L-amino acids, because of amino acid alpha carbon chirality. The D-amino acid form of L1AD3 is synthesized sequentially in the opposite direction from that of the L1AD3 peptide (from amino terminus to carboxyl terminus, rather than the conventional COOH to $NH_2$ progression used for synthesizing peptides with L-amino acids) Seq. ID No. 6. This process of synthesis using D-amino acids is sometimes called "retro-inversion" (Van Regenmortel and Muller, 1998). In this way the entire D-amino acid L1AD3 peptide is exactly superimposable with the L-amino acid L1AD3 peptide, except for the orientation of the carbonyl and N-H moieties that constitute each CONH peptide bond. This D-amino acid peptide thus avoids the proteolytic enzymes of the body's cells that might degrade the corresponding L-amino acid peptide and also avoids removal by the body's immune system (Herve et al., 1997; Bonnie et al., 2001).

Moreover, the D-amino acid peptide works in exactly the same manner as that of the L-amino acid L1AD3 peptide due to the fact that the side chains of both versions are completely and exactly superimposable. It is believed that the D-amino acid peptide has the same activity and potency against leukemic T-cells and the cell receptor. In many cases, D-amino acid peptides are as active or more active than their L-amino acid peptide counterparts (Kaneda et al., 1997).

The D-amino acid peptides corresponding to the above L-form peptides, and their Seq. ID numbers are as follows:

Cys-Thr-Lys-Tyr-Phe-Leu-Pro-Val-Leu-Lys-Asn-Cys-Lys-Leu [single letter code: CTKYFLPVLKNCKL] Seq. ID No. 6, the D-amino acid form of the Seq. ID No.1.

Cys-Thr-Lys-Tyr-Phe-Leu-Pro-Ile-Leu-Lys-Asn-Cys-Lys-Leu [single letter code: CTKYFLPILKNCKL] Seq. ID No. 7, the D-amino acid form of the Seq. ID No.2.

Cys-Thr-Lys-Tyr-Ala-Leu-Pro-Ile-Leu-Lys-Asn-Cys-Lys-Leu [single letter code: CTKYALPILKNCKL] Seq. ID No. 8, the D-amino acid form of the Seq. ID No.3.

Cys-Thr-Lys-Tyr-Ala-Leu-Pro-Val-Leu-Lys-Asn-Cys-Lys-Leu [single letter code: CTKYALPVLKNCKL] Seq. ID No. 9, the D-amino acid form of the Seq. ID No.4.

Cys-Thr-Lys-Tyr-Phe-Leu-Pro-Val-Leu-Lys-Gln-Cys-Lys-Leu [single letter code: CTKYFLPVLKQCKL] Seq. ID No. 10, the D-amino acid form of the Seq. ID No.5.

In yet another aspect, the present invention relates to the L1AD3 peptide and all its variations mentioned herein, along with the other peptides, their variations, and similar counterparts that require cyclization, (oxidation between the two terminal Cys residues) in order for them to show maximal potency and binding activity towards leukemic T-Cells, B-cells, or any other type of cancer cell.

The secondary and tertiary structures of these peptides occur nowhere in nature, due to the orientation of the disulfide bond formed upon cyclization between the only two Cys amino acid residues, which are located near the termini of their primary sequences. The D-amino acid side chains are superimposable with the L-amino acid side chains of these peptides because both forms have the exact overall secondary and tertiary structure. These D and L amino acid residues, on their respective peptides, have the same side-chain orientation with respect to each other and to their external environment. The difference in orientation occurs only in the sequence of the carbonyls and N—H groups. As a consequence of the very similar orientation of amino acid side chains, the D-amino acid L1AD3 type peptides of the present invention are believed to have the same cytotoxic properties toward leukemic T-cells, as well as binding properties toward the cell receptor target, as the L-amino acid L1AD3 peptide. The fact that the two peptide sequences run in opposite directions makes them different peptides. It is only when the two peptides are superimposed that they both appear to have the same primary structures.

The D-amino forms of these peptide sequences are significant because the proteolytic enzymes of the liver and pancreas are bypassed: digestive proteases are only capable of breaking amide (peptide) bonds between L-amino acid residues and not between D-amino acid residues.

Yet another aspect of the present invention relates to analogous peptides in which only one or a subset of individual L-amino acid residues have been replaced by corresponding D-amino acids, which optimizes potency and/or selectivity.

Still another aspect of the present invention relates to the use of at least one of the peptides, or a portion thereof, to facilitate the identification of cancer cells. In one aspect, the biotin "handle" on loop analogs is useful to identify cancer cells since, for example, Loop 1 binds leukemic T-lymphocytes but not normal human T-lymphocytes.

EXAMPLES

The peptide called L1AD3, Seq. ID No. 1, prevents the proliferation of cancerous human T-lymphocytes (CEM cell line) by inhibiting incorporation of thymidine into DNA. At peptide concentrations between 0.625 μM and 40 μM, incorporation of tritiated thymidine is reduced from 13% to 99.7%, respectively, in a four-hour assay.

The L1AD3 peptide, Seq. ID No. 1, induces the exposure of phosphatidyl serine on the outer surface of CEM cells and Jurkat cells (another human T-lymphocyte cancer cell line) but does not make the cells permeable either to ethidium bromide or to propidium iodide. This combined assay is widely accepted as a measure of cell death by a process known as apoptosis. It is believed that induction of apoptosis rather than induction of the more catastrophic form of cell death, termed necrosis, is desirable in a potential cancer chemotherapeutic agent in order to facilitate removal of dead target cells by phagocytes instead of stimulating a patient's inflammatory response.

Flow cytometry using fluorescent Annexin-V distinguishes cells with externalized phosphatidyl serine. As long as the cell's plasma membrane remains intact, fluorescent dyes such as ethidium bromide or propidium iodide are excluded. A 40 μM concentration of L1AD3 caused approximately 93% of CEM cells to become Annexin-V-positive within 2.5 hours, which is unusually short for signs of apoptosis to occur. Camptothecin, a cancer chemotherapeutic agent administered in control experiments at 20 μM, caused only 33% of the cells to appear apoptotic. While neither L1AD3 nor camptothecin caused increases in cell permeability to propidium iodide, the "parent" cardiotoxin at 10 μM concentrations induced permeability within 30 seconds of application, as viewed by fluorescence microscopy.

The L1AD3 peptide composition, Seq. ID No. 1, did not induce externalization of phosphatidyl serine by normal human white blood cells. It also has no permeabilizing effect on normal human cells in the presence of propidium iodide, ethidium bromide or trypan blue. In addition, binding studies using biotinylated L1AD3 and CEM cells showed essentially 50% inhibition by non-biotinylated L1AD3. By contrast, apparent binding to normal human white blood cells was less than the CEM cell background in the absence of biotinylated L1AD3 (meaning there is no appreciable binding of the L1AD3 peptide to normal human white blood cells). It is believed that there is an absence of the L1AD3 protein receptor on the surface of normal human white blood cells, whereas the L1AD3 protein receptor target is found in the surface of leukemic T-cells. Further studies using cardiac myocytes indicated that a 2-hour incubation with 40 μM L1AD3 had no effect upon the beating of the heart cells, whereas 1 μM of the "parent" cardiotoxin caused the heart cells to stop beating within 10–30 seconds.

With regard to the existence of a protein cell-surface receptor for L1AD3, Seq. ID No. 1, biotinylated L1AD3 bound human cancer cells, but that binding was abolished if the cells were pre-treated with the enzyme trypsin, which digests proteins. In other experiments, when cells that had bound biotinylated L1AD3 were treated with different cross-linking reagents and then disrupted and subjected to a modified Western blotting procedure using avidin-horseradish peroxidase, a protein was visualized with an approximate molecular weight of 27–35 kDa. Such a cell-membrane protein is useful as a novel target for delivery of chemotherapeutic agents.

The peptide described in this invention, L1AD3, Seq. ID No. 1, is one of a set of synthetic cyclized peptides disclosed herein, which vary from the known sequences of cobra cardiotoxins. It now has been discovered by the inventors herein that, by analysis of sequence and activity data from whole cardiodtoxins, an asparagine at position 4 and a tyrosine at position 11 in the 14-mer are desired for activity. Computer modeling data confirmed the requirement for both a phenyl ring and a hydroxyl on the tyrosine side chain to be oriented perpendicular to the backbone and directed outward from it. Also, if Asn at position 4 were substituted with Lys (as in the case of *Naja naja oxiana,* which is inactive) or with His (as in the case of *Naja haje annulifera* cardiotoxins), the distance between the arms of the loop connecting the beta strands was widened by 1–2 Angstroms, which, it is believed, hinders the ability of peptide analogs to bind to the protein receptor described above. The L1AD3 peptide is therefore useful as a lead compound for the development of a new set of chemotherapeutic agents.

The D-amino acid L1AD3 peptide and the variations described above also have comparable activity and potency properties as described herein.

The amino acid sequence of the 14-mer L1AD3 peptide developed, synthesized and tested by the inventors herein is: Leu-Lys-Cys-Asn-Lys-Leu-Val-Pro-Leu-Phe-Tyr-Lys-Thr-Cys [single letter code: LKCNKLVPLFYKTC] Seq. ID No. 1. In the parent 60-amino acid cytotoxin (CTX, Seq. ID No. 11) purified from the Taiwan cobra, *Naja naja atra,* these 14 amino acids at the N-terminal constitute the first loop of the three-loop protein. In the peptide analog of Loop 1, L1AD3, Seq. ID No. 1, L1 refers to Loop 1, A refers to its origin from *N. n. atra,* D refers to the Dufton & Hider class D of cytotoxins, and 3 indicates that more particularly it is derived from CTX-III. This peptide was synthesized and then was cyclized after hplc purification, see FIG. 2, by facilitating the formation of a disulfide bridge between cysteines at positions 3 and 14 (see Table II, which reflects the use of Ellman's reagent to demonstrate the oxidation that occurs during the disulfide bond formation).

TABLE II

Ellman's reagent test of peptide disulfide bond formation

| Sample Name | UV Absorption λ = 412 nm |
|---|---|
| L1AD3 (Seq. ID No. 1) | 0.005 |
| BTN L1AD3 (Seq. ID No. 12) | 0.006 |
| L1 Y − S AD3 (Seq. ID No. 13) | 0.001 |
| L1 Y − F AD3 (Seq. ID No. 14) | 0.002 |
| L1 Y − W AD3 (Seq. ID No. 15) | 0.004 |
| L1 K + S AD3 (Seq. ID No. 18) | 0.019 |
| L1 N − K AD3 (Seq. ID No. 16) | 0.010 |
| L1 N − H AD3 (Seq. ID No. 17) | 0.033 |
| DTNB Control | 0.006 |
| Free Sulfhydryl (Cys) | 1.830 |
| Oxidized Sulfhydryl (Cys—Cys) | 0.005 |
| Linear L1AD3 (negative contro | 0.444 |

Figure 3:
FIG. 3 is a biotin-avidin sorbant assay (modified Western blot) of cyclized (left lane) and linear (right lane) biotinylated L1AD3. The blot indicates that only monomeric peptides are formed, since the single non-reduced band migrates the same distance as the single reduced band. Furthermore, the presence of N-terminal biotin is indicated by the ability of each peptide to bind avidin-HRP and subsequently convert substrate to a chemiluminescent product.

Sodium dodecyl sulfate polyacrylamide gel electrophoresis under reducing and non-reducing conditions also indicated that the peptide was monomeric (see FIG. 3, which shows a Western blot of reduced and linear biotinylated L1AD3 that indicates cyclization without the formation of homopolymers). Amino acid compositional analysis and mass spectrographic analysis confirmed the success of the synthetic procedure (see FIGS. 4 and 5, which show the mass spec data in which 2 mass units are lost during cyclization, and confirm the identity of the peptide). It should be noted that in CTX, the native disulfide bridges involving Cys-3 and Cys-14 are not between each other, but rather Cys-3 bridges to Cys-21 and Cys-14 bridges to Cys-38. Thus the L1AD3 peptide, Seq. ID No. 1, is not identical to the N-terminal of CTX. Therefore, L1AD3 peptide and its D-amino acid form and other variants are unique and not found in nature.

Figure 6:
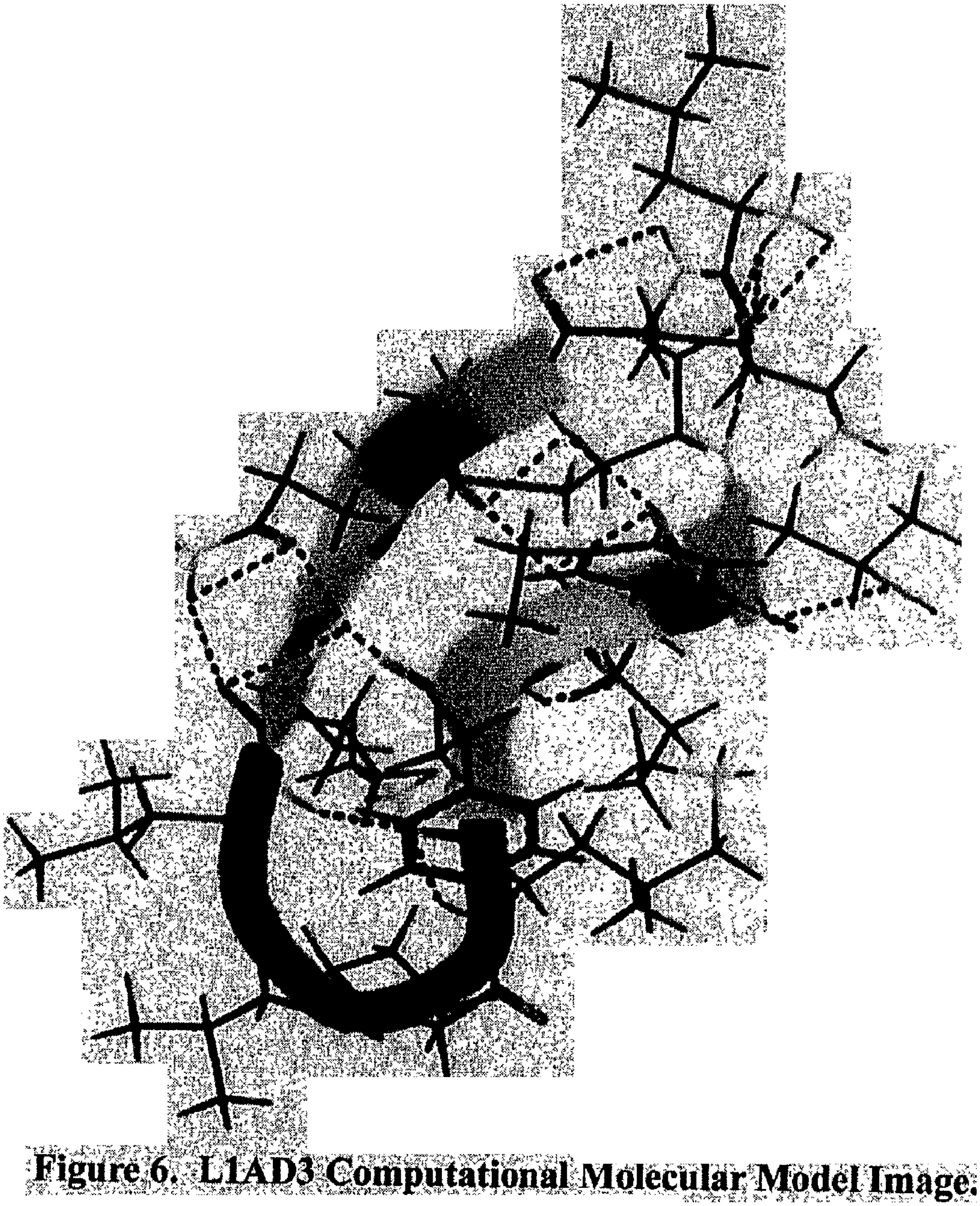
FIGS. 6 and 7 are molecular models of L1AD3 and of L1AD3 superimposed with an analog in which Asn at position 4 is replaced with Lys. Note the widening of the yellow strand in the analog, which could hinder this modified peptide from fitting into a receptor binding crevice.
Figure 7:
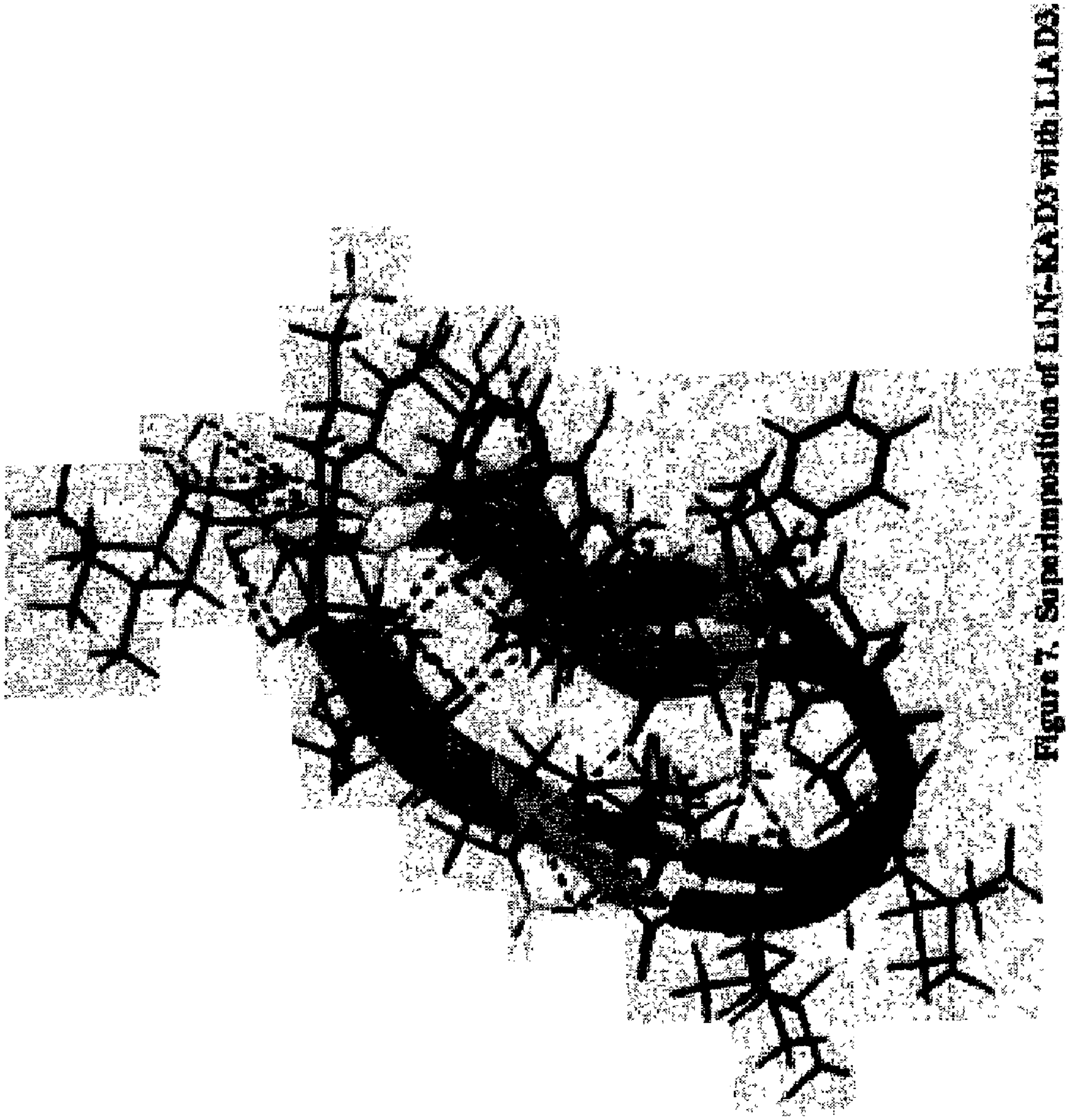

Molecular modeling of the L1AD3 peptide and 7 other analogs was based upon the coordinates obtained from the Brookhaven Protein Data Bank for the crystal structure of CTX-III of *N. n. atra*. The Sybyl Program version 5.5C was used. The 46 residues that follow Loop 1 were deleted and a disulfide bond was created between residues 3 and 14. Charges were set using Kollman All-Atom Force Field charge numbers. Energies were established using the Kollman All-Atom AMBER United Force Field, both in vacuo and in liquid phase, using a pre-computed $H_2O$ periodic solvent box. Once the overall molecular energy was computed, the molecule's energy was minimized using the Maxim2 algorithm, Powell Method. Typically the algorithm used 10,000 iterations, and the minimization was repeated three times to ensure that the peptide was at a global energy minimum and not at a local minimum. Structural features of the L1AD3 peptide are seen in FIGS. 6 and 7, where the blue ribbons reflect the beta strands that form a beta sheet, involving amino acids 1–5 and 10–14, and the yellow represents the joining amino acid residues in positions 6–9. The side chain of Tyr-11 is oriented perpendicular to the beta sheet backbone where it can readily interact with solvent or with a target cell receptor.

In contrast to the activity of the parent CTX, which at micromolar concentrations drastically perturbs the plasma membrane of various murine and human cancer cells, within seconds rendering them permeable to trypan blue or to fluorescent dyes such as ethidium bromide or propidium iodide, the L1AD3 peptide does not permeabilize cells from either the Jurkat or the CEM human leukemic T-lymphocyte line.

Figure 8:
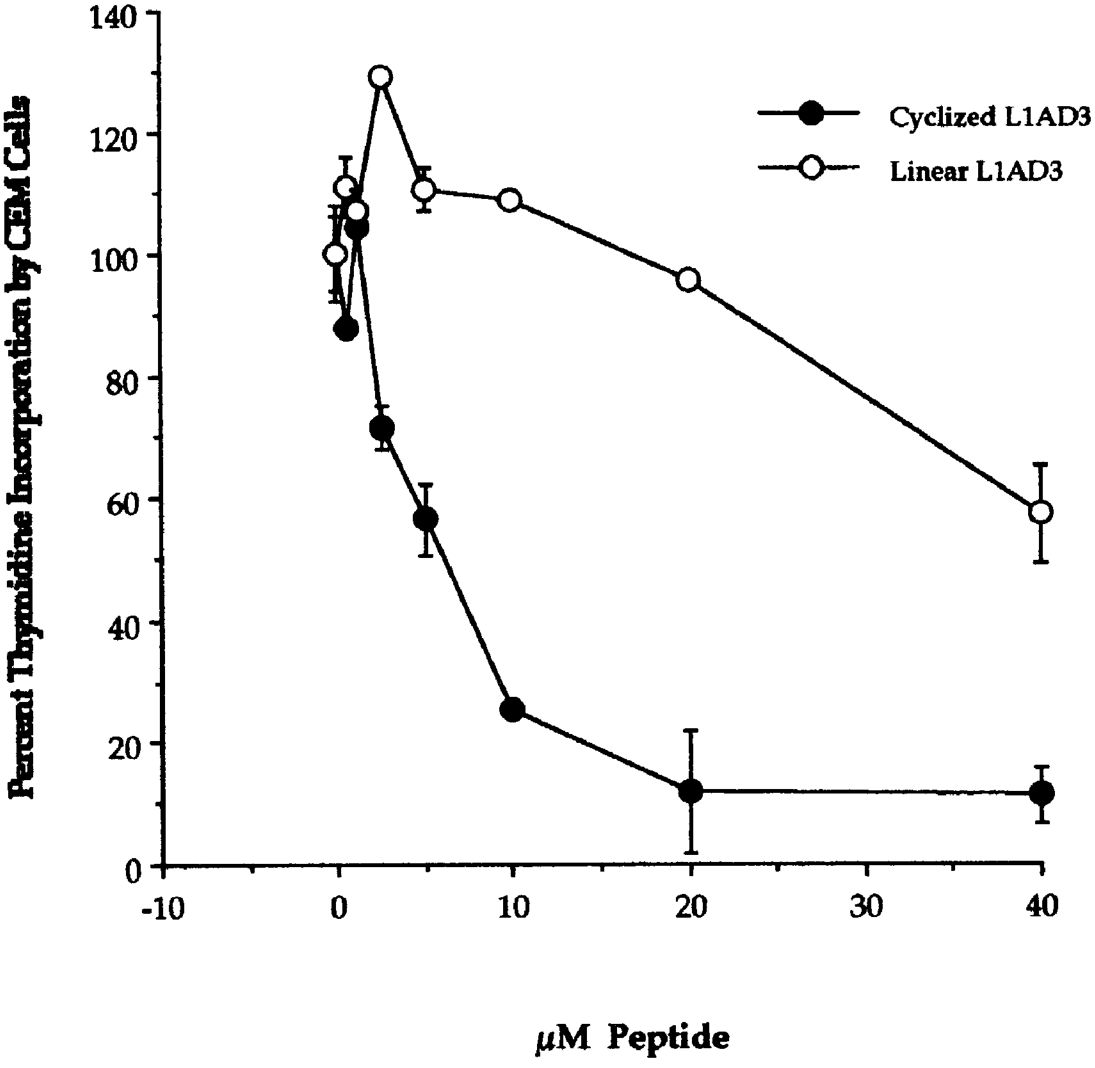
FIG. 8 is a graph showing percent inhibition of thymidine incorporation as a function of peptide concentration. Each well of a microtiter plate received 200,000 CEM cells in log phase of growth, suspended in 50 μl complete medium. The same volume of diluted peptide, either linear or cyclized, was added to achieve the final concentrations shown. After a 1 -hour incubation at 37 degrees C., 1 μCi of $[^3H]$-thymidine in 25 μl medium was added, and the plates were incubated another 3 hours prior to harvesting. Control cells were incubated without either peptide, but with the same volume of medium.

The L1AD3 peptide stops tumor cell division in both Jurkat and CEM cells with an $EC_{50}$ of approximately 5 μM, as shown in FIG. 8. This is indicated by the inhibition of thymidine incorporation into DNA. This is approximately ten times the CTX $EC_{50}$ upon mouse L1210 cells or human CEM cells (Hinman, Jiang and Tang, 1990). The $EC_{50}$ of the non-cyclized, linear peptide is more than eight times that of its cyclized counterpart, about 43 μM. In contrast to CTX, which rapidly depolarized skeletal muscle (Dufton and Hider, 1991), and which at 1 μM concentrations causes cessation of beating of embryonic chicken heart cells within 5–10 seconds, the L1AD3 peptide at 40 μM concentrations has no effect upon the beating of heart cells over 2 hours of observation. Therefore, it is believed that the L1AD3 peptide, along with the other seven peptides, is not harmful to the heart, in contrast to native CTX.

Figure 9:
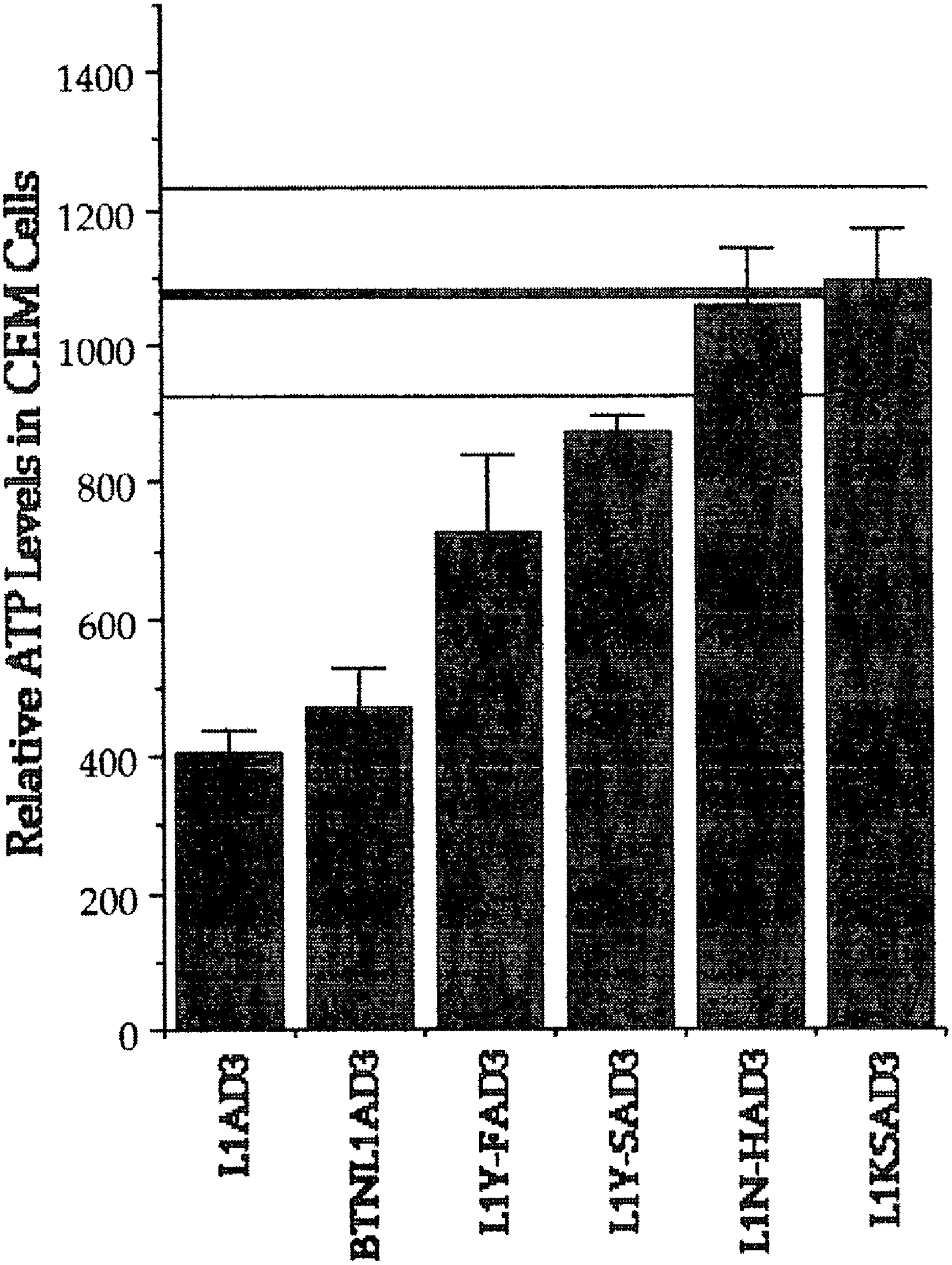
FIG. 9 is a graph showing the amounts of total ATP present in cell lysates following incubation of CEM cells with peptide analogs. Cyclized peptides were added at double their final concentration, which was 20 μM, to triplicate wells of a black 96-well reaction plate. CEM cells (50,000 per well) were added in the same volume, and the plate was incubated 30 minutes at 37 degrees. Lysis buffer (Sigma) was added, followed by luciferin/luciferase assay buffer (Molecular Probes). The plate was sealed with a clear plastic film and read using a Packard Top-Count reader. Cells with medium only had ATP levels of 1073±160 in arbitrary luminescence units. Peptide analogs are identified by single amino acid modifications.

Changes in cellular energy levels can contribute to the process of cytotoxicity. ATP was measured using a 96-well luciferin/luciferase bioluminescence assay system and found a 60% reduction in ATP after 30 minutes' incubation of CEM cells with 20 μM L1AD3, as shown in FIG. 9. While somewhat large, this reduction of ATP is consistent with apoptosis, inasmuch as necrosis tends to occur when ATP levels drop to below 30% of control.

The peptide of this invention, L1AD3, enhances the binding of fluorescent Annexin-V to tumor cell membranes without increasing permeability to propidium iodide, which shows that this peptide induces apoptosis (Martin et al., 1995; Zhang et al., 1997). CEM cells were incubated for one hour with 40 μM peptide, washed twice, and then incubated with Annexin-V-FITC. The entire procedure, including flow cytometric analysis, took about 2.5 hours. Within that time, more than 80% of the cells were positive for Annexin-V binding, compared with less than 6% of untreated cells, as shown in FIGS. 10*a–d*. Treatment with a high dose of camptothecin (20 μM) only produced 23% apoptosis, which is comparable with results of a previous study using HL-60 cells (Fernandes and Cotter, 1994). Normal human peripheral white blood cells (PBL's) were not affected above background levels (less than 5%) by exposure to the same concentration of peptide. In other experiments, after a 1-hour incubation with L1AD3, when PBL's were double-labeled with biotinylated Annexin-V and with FITC-labeled lymphocyte-specific monoclonal antibodies (anti CD-3 for pan-T-cells; anti CD-19 for B-cells; anti CD-14 for macrophages) followed by incubation with tetramethyl-rhodamine-conjugated NeutrAvidin, no preference for one cell type above another was observed: all were within background levels.

Figure 11:
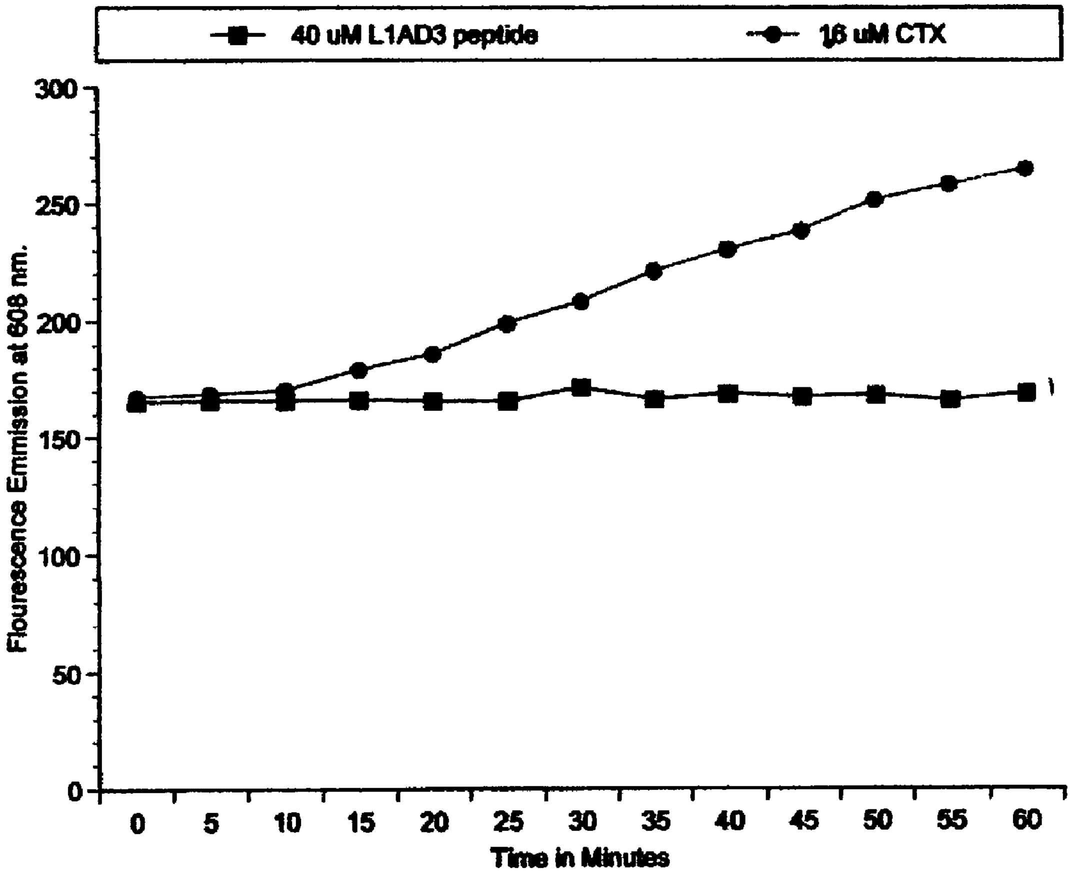
FIG. 11 is a graph showing changes in cell permeability to ethidium bromide following incubation with L1AD3 or with native CTX. CEM cells ($10^6$/ml) were incubated in quartz cuvets in a Shimidzu fluorescence spectrophotometer with 1 μg/ml ethidium bromide. Either CTX at a final concentration of 1.6 μM or L1AD3 at a final concentration of 40 μM was added, and readings were taken at 5-minute intervals, with excitation at 526 nm and emission measured at 608 nm.

Since whole CTX can rapidly permeabilize leukemic T-lymphocytes, separate experiments using a fluorescence spectrophotometer were applied to examine changes in plasma membrane permeability to ethidium bromide following exposure of CEM cells either to L1AD3 or to CTX. In the presence of 1.6 μM CTX, cells began to admit ethidium bromide within 15 minutes; in the presence of 40 μM L1AD3, cells remained impermeable for 2 hours. Results from a 1-hour experiment are shown in FIG. 11. When cells were examined using propidium iodide and acridine orange under fluorescence microscopy, similar results were obtained: cells treated with L1AD3 remained impermeable (green fluorescence due to binding of acridine orange); cells treated with CTX rapidly became permeable (green replaced by yellow, then orange-red, as the propidium iodide displaced acridine orange from its binding sites on DNA).

Figure 12:
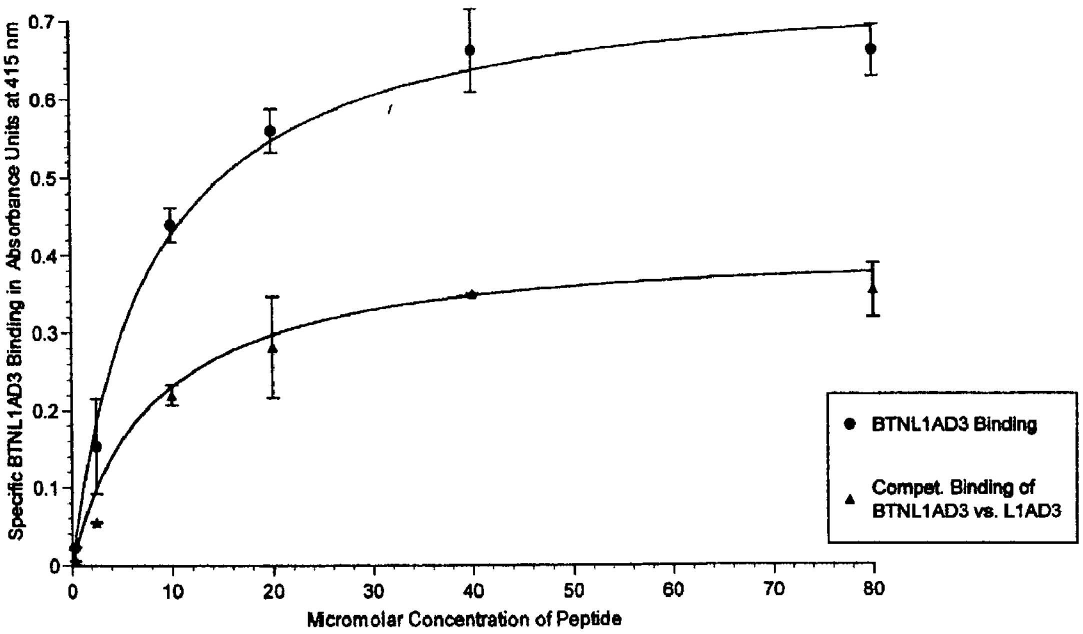
FIG. 12 is a graph showing inhibition of specific binding of biotinylated L1AD3 by non-biotinylated L1AD3. CEM cells were held on the surface of 96-well plates previously coated with anti-human MHC-1 antibody (anti-HLA-A,B, C). After plates containing adherent cells were blocked with bovine albumin and washed with PBS, biotinylated L1AD3, either alone (upper trace) or in a 1:1 ratio with non-biotinylated L1AD3 (lower trace), was added to triplicate wells to achieve the indicated final concentrations. After a 1-hour incubation at 37 degrees, plates were washed three times with PBS, and avidin-HRP was added. Enzyme substrate (ABTS) was added, and color development at 415 nm was monitored using an ELISA plate reader with printed output.

To investigate peptide binding to cell surfaces, the peptide was modified by N-terminal biotinylation. This was accomplished after the last amino acid was added during synthesis, while the protected peptide was still on the resin. Decoupling and hplc purification were followed by mass-spectrographic analysis to confirm the molecular mass. An assay involving 4-hydroxyazobenzene-2-carboxylic acid (HABA), performed to verify the presence of D-biotin on the peptide indicated 100% biotinylation. A biotin-avidin sorbant assay, similar to an ELISA procedure was performed to measure binding. In this assay, horseradish peroxidase-conjugated avidin was employed rather than an enzyme-linked second antibody. Mouse anti-human MHC-1 (anti HLA-A,-B,-C) antibody was used to hold CEM or normal human cells to the surface of 96-well microtiter plates. The binding of biotinylated peptide to CEM cells is saturable, with an apparent $K_D$ of about 6 μM. When added in equimolar amounts (L1AD3 and biotinylated L1AD3 at a 1:1 ratio), the unlabeled peptide competitively inhibited the binding of biotinylated peptide, with a 47% reduction of binding, as shown in FIG. 12, indicating that L1AD3 and biotinylated L1AD3 bind the same receptor site. Biotinylated L1AD3, however, did not bind appreciably to normal human PBL's, either in the presence or absence of non-biotinylated L1AD3. When binding was measured by fluorescence spectroscopy using CEM cells in suspension, along with avidin-FITC, fluorescence increased by 48% over cells not incubated with biotinylated peptide prior to washing.

Figure 13:
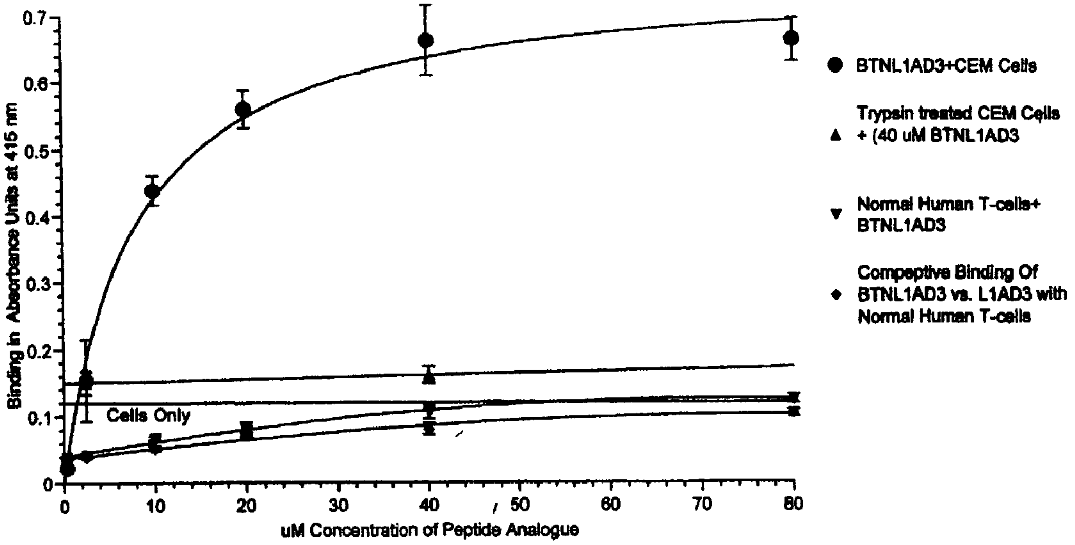
FIG. 13 is a graph showing inhibition of specific binding of biotinylated L1AD3 to normal human peripheral blood lymphocytes by non-biotinylated L1AD3, and abolition of binding by pretreatment of CEM cells with trypsin. The lower two traces in the figure were developed as described above for FIG. 12, except that the target cells were human PBL's that had been isolated about 4 hours before the assay. The upper two traces indicate the ability of trypsin to prevent L1AD3 binding to CEM cells. In this case, 0.0125% trypsin was incubated with adherent cells for 10 min, followed by three washes and subsequent addition of soybean trypsin inhibitor. In separate experiments, this pretreatment was found not to affect cell viability (measured by trypan blue exclusion), nor did it alter the character of L1AD3 (measured by hplc).

In order to investigate the nature of the binding site for L1AD3 on tumor cells, trypsin was added to the cells and subsequently quenched by adding enzyme inhibitor prior to measurements of binding, using biotinylated peptide in either the solid-phase or the fluorescent assay described above. Protease pretreatment abolished binding of the peptide in both assays, suggesting that the binding site on the cell surface is a protein, as shown in FIG. 13. By using two different fluorescent labels on avidin, FITC or tetramethylrhodamine (TMR), it was possible to estimate the distance between binding sites on the cell membrane by a fluorescence resonance energy transfer assay (FRET). Since the optimal emission wavelength spectrum of FITC (maximum at 520 nm) overlaps with the absorption spectrum of TMR (maximum at 545 nm), if two molecules bearing different labels are within their Foerster radius (55 Angstroms in the case of these two dyes), there will be a transfer of light energy following the excitation of FITC at 488±5 nm to the other probe, labeled with TMR. Emission from the tetramethylrhodamine at 580 nm will thus occur only when the two biotinylated peptides are within 55 Angstroms and one binds avidin-FITC, while the other binds avidin-TMR. Approximately 10,000 cells were measured using flow cytometry. The measurement of significant fluorescence at 580 nm for biotinylated CTX suggests that CTX binding sites are within 55 Angstroms of each other, while the absence of fluorescence energy transfer for biotinylated L1AD3 at 580 nm suggests that peptide binding sites are more than 55 Angstroms apart and that perhaps the two peptides bind to different kinds of acceptor sites.

Bifunctional crosslinking reagents have been applied to cells after their incubation with biotinylated peptide, followed by gel electrophoresis and a modified Western blotting procedure, using horseradish peroxidase-conjugated avidin, this time in an enhanced chemiluminescence assay, to determine an approximate size of the protein on the CEM cell surface that binds L1AD3. The receptor protein has a molecular weight between 27 and 35 kDa.

It should be noted that in addition to L1AD3, the principal subject of this invention, seven additional analogs of CTX Loop 1 were synthesized, modeled, and tested in the above-described assays. These analogs and their sequence ID Nos. are as follows:

Biotin-Leu-Lys-Cys-Asn-Lys-Leu-Val-Pro-Leu-Phe-Tyr-Lys-Thr-Cys [single letter code: btn-LKCNKLVPLFYKTC] Seq. ID No. 12, where the N-terminal Leu is biotinylated during synthesis of Seq. ID No. 1.

Leu-Lys-Cys-Asn-Lys-Leu-Val-Pro-Leu-Phe-Ser-Lys-Thr-Cys [single letter code: LKCNKLVPLFSKTC] Seq. ID No. 13, where, at position 11, Tyr is replaced by Ser in Seq. ID No. 1.

Leu-Lys-Cys-Asn-Lys-Leu-Val-Pro-Leu-Phe-Phe-Lys-Thr-Cys [single letter code: LKCNKLVPLFFKTC] Seq. ID No. 14, where, at position 11, Tyr is replaced by Phe in Seq. ID No. 1.

Leu-Lys-Cys-Asn-Lys-Leu-Val-Pro-Leu-Phe-Trp-Lys-Thr-Cys [single letter code: LKCNKLVPLFWKTC] Seq. ID No. 15, where, at position 11, Tyr is replaced by Trp in Seq. ID No. 1.

Leu-Lys-Cys-Lys-Lys-Leu-Val-Pro-Leu-Phe-Tyr-Lys-Thr-Cys [single letter code: LKCKKLVPLFYKTC] Seq. ID No. 16, where, at position 4, Asn is replaced by Lys in Seq. ID No. 1.

Leu-Lys-Cys-His-Lys-Leu-Val-Pro-Leu-Phe-Tyr-Lys-Thr-Cys [single letter code: LKCHKLVPLFYKTC] Seq. ID No. 17, where, at position 4, Asn is replaced by His in Seq. ID No. 1.

Leu-Lys-Cys-Lys-Lys-Leu-Val-Pro-Leu-Phe-Ser-Lys-Thr-Cys [single letter code: LKCKKLVPLFSKTC] Seq. ID No. 18, where, at position 4 Asn is replaced by Lys and at position 11, Tyr is replaced by Ser in Seq. ID No. 1.

These examples show the importance of Tyr at position 11 and of Asn at position 4 in Loop 1 of CTX. Amino acid substitutions that altered the length of the hydroxyl-carrying tyrosine side chain, or that deleted either the phenyl ring or the hydroxyl group eliminated activity. Substitution of Ser for Tyr at position 11, for example, resulted in a peptide in which the side chain pointed toward the inside of the beta sheet instead of outward and perpendicular to it, forming a new hydrogen bond with the N—H of the opposite beta strand backbone, and which proved to be inactive in biological tests. Substitutions that widened the distance between the arms of the random coil connecting the beta strands of Loop 1 also strongly affected the activity of the resulting peptide.

These examples show that L1AD3 is useful as a lead compound for the development of further anti-cancer agents. In addition, peptides with D-amino acids are believed to retain the ability to bind to L1AD3's surface receptor. In another type of chemical modification, it is shown that biotinylation of L1AD3 preserves its ability to bind cancer cells, and retains its ability to reduce ATP levels in cancer cells, even though other activities are significantly diminished. Thus, still other uses of analogs of L1AD3 include delivery of drugs or other agents to the same cancer cell target by virtue of the retention of binding by modified peptide.

The foregoing description of the invention is illustrative and explanatory thereof, and many variations will occur to those in the art. It is intended that all such variations within the scope and spirit of the appended claims be embraced thereby.

The above detailed description of the present invention is given for explanatory purposes. It will be apparent to those skilled in the art that numerous changes and modifications can be made without departing from the scope of the invention. Accordingly, the whole of the foregoing description is to be construed in an illustrative and not a limitative sense, the scope of the invention being defined solely by the appended claims.

REFERENCES

The references discussed above and the following references, to the extent that they provide exemplary procedural or other details supplementary to those set forth herein, are specifically incorporated herein by reference.

| | | |
|---|---|---|
| Vidal | 5,232,911 | August 1993 |
| Plata et al. | 5,164,196 | Nov. 17, 1992 |
| Lipps et al. | 5,565,431 | October 1996 |

1. Bonnie C., Oberson A., Negri S., Sauser C., and Schorderet D. F. (2001) "Cell-permeable peptide inhibitors of JNK novel blockers of beta-cell death." Diabetes 50 (1): 77–82.
2. Dufton, M. J. and Hider, R. C. (1991) "The Structure and Pharmacology of Elapid Cytotoxins," In: *Snake Toxins* [A. L. Harvey, Ed.] New York: Pergamon Press, pp 259–302.
3. Fernandes, R. S. and Cotter, T. G. (1994) "Apoptosis or necrosis-intracellular levels of glutathione influence mode of cell death." Biochemical Pharmacology 48(4): 675–681.
4. Gatineau, E., Takechi, M., Bouet, F., Mansuelle, P., Rochat, H., Harvey, A. L., Montenay-Garestier, Th. and Menez, A. (1990) "Delineation of the functional site of a snake venom cardiotoxin: preparation, structure, and function of monoacetylated derivatives." Biochemistry 29: 6480–6489.
5. Gatineau, E., Toma, F., Montenay-Garestier, Th., Takechi, M., Fromageot, P. and Menez, A. (1987) "Role of tyrosine and tryptophan residues in the structure-activity relationships of a cardiotoxin from *naja nigricollis* venom." Biochemistry 26: 8046–8055.
6. Herve M., Maillere B., Mourier G., Texier C., Leroy S., and Menez A. (1997) "On the immunogenic properties of retro-inverso peptides. Total retro-inversion of T-cell epitopes causes a loss of binding to MHC II molecules." Mol Immunol. 34(2):157–63.
7. Hinman, C. L., Jiang, X. L. and Tang, H. P. (1990) "Selective cytolysis by a protein toxin as a consequence of direct interaction with the lymphocyte plasma membrane." Toxicology & Applied Pharmacology 104: 290–300.
8. Kaneda, Y., Yamamoto, Y., Okada, N., Tsutsuml, Y., Nakagawa, S., Kakiuch, M., Maeda, M., Kawasaki, K., and Mayumi, T. (1997) "Antimetastatic effect of synthetic Glu-Ile-Leu-Asp-Val peptide derivatives containing D-amino acids." Anticancer Drugs 8(7):702–7.
9. Kini, R. M. and Evans, H. J. (1989) "Role of cationic residues in cytolytic activity: modification of lysine residues in the cardiotoxin from *Naja nigricollis* venom and correlation between cytolytic and antiplatelet activity." Biochemistry 28: 9209–9215.
10. Lin, S. R., Chang, K. L. and Chang, C. C. (1993) "Chemical modification of amino groups in cardiotoxin-III from Taiwan cobra (*Naja naja atra*) venom." Biochemistry & Molecular Biology International 31: 175–184.
11. Martin, S. J., Reutelingsperger, C. P. M., McGahon, A. J., Rader, J. A., Vanschie, R. C. A. A., Laface, D. M. and Green, D. R. (1995) "Early redistribution of plasma-membrane phosphatidylserine is a general feature of apoptosis regardless of the initiating stimulus—inhibition by overexpression of Bcl-2 and Abl." Journal of Experimental Medicine 182(5): 1545–1556.
12. Stevens-Truss, R., Messer, W. S., Jr. and Hinman, C. L. (1996) "Heart and T-lymphocyte cell surfaces both exhibit positive cooperativity in binding a membrane-lytic toxin." Journal of Membrane Biology 150:113–122.
13. Stevens-Truss, R. and Hinman, C. L. (1996) "Chemical modification of methionines in a cobra venom cytotoxin differentiates between lytic and binding domains." Toxicology & Applied Pharmacology 139: 234–242.
14. Stevens-Truss, R. and Hinman, C. L. (1997) "Activities of cobra venom cytotoxins toward heart and leukemic T-cells depend on localized amino acid differences." Toxicon 35: 659–669.
15. Van Regenmortel, M. H., and Muller, S. (1998) "D-peptides as immunogens and diagnostic reagents." Curr. Opin. Biotechnol. 9(4): 377–82.
16. Zhang, G. H., Gurtu, V., Kain, S. R. and Yan, G. C. (1997) "Early detection of apoptosis using a fluorescent conjugate of Annexin-V." Biotechniques 23 (3 September): 525 & ff.

We claim:

1. A composition of matter comprising a cyclic peptide, 14 amino acids in length with a disulfide bond between residues 3 and 14 (Cys 3 and Cys 14) which consists of the following sequence: Leu-Lys-Cys-4-Lys-Leu-7-Pro-Leu-10-Tyr-Lys-Thr-Cys, where 4 is Asn or Gln; 7is Val or Ile; 10 is Phe or Ala having the SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, and SEQ ID NO:12.

2. A composition comprising the cyclic peptide, 14 amino acids in length with a disulfide bond between residues 3 and 14 (Cys 3 and Cys 14) which consists of the following sequence: Leu-Lys-Cys-4-Lys-Leu-7-Pro-Leu-10-Tyr-Lys-Thr-Cys, where 4 is Asn or Gln; 7is Val or Ile; 10 is Phe or Ala, having the SEQ ID NO:1, SEQ ID NO:2, SEQ ID NO:3, SEQ ID NO:4, SEQ ID NO:5, and SEQ ID NO:12, in which at least one amino acid is replaced with its corresponding D-amino acid.

3. The composition of claim 1 useful as a cytotoxic agent against leukemic T-cells and B-cells.

4. A composition comprising the cyclic peptide from claim 1, for inducing apoptosis in cancer cells, leukemic T-cells and B-cells.

5. A composition comprising the cyclic peptide from claim 2, for inducing apoptosis in cancer cells, leukemic T-cells and B-cells.

6. A peptide selected from the group consisting of SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, and SEQ ID NO:12, or a physiologically acceptable salt thereof, and wherein said peptide is capable of exhibiting cytotoxic activity.

7. A composition of matter comprising at least one peptide of claim 1 and a vehicle, and wherein said composition of matter is capable of exhibiting cytotoxic activity.

8. The composition of claim 1, wherein the cytotoxic activity is against at least one of T-cells and B-cells.

9. A peptide selected from the group consisting of SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, and SEQ ID NO:12 or a physiologically acceptable salt thereof, and wherein said peptide is capable of inducing apoptotic activity in cancer cells.

10. The peptide of claim 6, wherein the peptide is capable of inducing apoptotic activity in at least one of T-cells and B-cells.

11. The composition of claim 7, wherein the composition of matter is capable of inducing apoptotic activity in at least one of T-cells and B-cells.

* * * * *